United States Patent
Bor et al.

(10) Patent No.: US 12,376,937 B2
(45) Date of Patent: Aug. 5, 2025

(54) OPHTHALMIC SURGICAL MICROSCOPE WITH STROBOSCOPIC ILLUMINATION

(71) Applicant: Alcon Inc., Fribourg (CH)

(72) Inventors: Zsolt Bor, San Clemente, CA (US); Reza Khazaeinezhad, Lake Forest, CA (US); Mikhail Ovchinnikov, Dana Point, CA (US); Alireza Malek Tabrizi, Irvine, CA (US); Keith Watanabe, Irvine, CA (US)

(73) Assignee: Alcon Inc., Fribourg (CH)

( * ) Notice: Subject to any disclaimer, the term of this patent is extended or adjusted under 35 U.S.C. 154(b) by 807 days.

(21) Appl. No.: 17/507,584

(22) Filed: Oct. 21, 2021

(65) Prior Publication Data

US 2022/0183786 A1    Jun. 16, 2022

Related U.S. Application Data

(60) Provisional application No. 63/126,413, filed on Dec. 16, 2020.

(51) Int. Cl.
*A61B 90/30* (2016.01)
*A61F 9/008* (2006.01)
(Continued)

(52) U.S. Cl.
CPC ............ *A61B 90/30* (2016.02); *A61F 9/008* (2013.01); *F21S 10/06* (2013.01);
(Continued)

(58) Field of Classification Search
CPC ............ A61F 9/008; A61F 2009/00863; A61F 2009/00874; A61F 2009/00887; A61F 2009/00891; A61F 9/007; A61F 9/00709; A61F 9/00736; A61B 90/30; A61B 2090/306; A61B 2090/309;
(Continued)

(56) References Cited

U.S. PATENT DOCUMENTS 10,070,988 B2 *   9/2018   McDonell ........... A61F 9/00745
10,537,401 B2 *   1/2020   Dos Santos ............ A61B 90/30
(Continued)

OTHER PUBLICATIONS

Oshima Yusuke: "Chandelier Endoillumination in Vitreoretinal Surgery", Retina Today, Jan. 1, 2013 (Jan. 1, 2013), pp. 68-72, XP055879354, Retrieved from the Internet: URL:https://retinatoday.com/articles/2013-jan/chandelier-endoillumination-in-vitreoretinal-surgery.

*Primary Examiner* — Ahmed M Farah

(57) ABSTRACT

An ophthalmic system for visualization of interactions between ocular matter and a probe tip of a probe within or in contact with an ocular space of an eye includes: a visualization tool having a field of view that includes at least a portion of the ocular space of the eye where the probe tip interfaces with the ocular matter; and a stroboscopic illumination source configured to stroboscopically illuminate at least the portion of the field of view at an illumination frequency. A method of operating a stroboscopic illumination source during an ophthalmic surgical procedure includes: identifying an illumination source type of the stroboscopic illumination source; identifying a probe type; identifying a first procedure trigger; and operating the stroboscopic illumination source based on the probe type, the illumination source type, and the first procedure trigger.

7 Claims, 12 Drawing Sheets

(51) Int. Cl.
*F21S 10/06* (2006.01)
*A61B 18/00* (2006.01)
*F21W 131/20* (2006.01)

(52) U.S. Cl.
CPC .............. *A61B 2018/00982* (2013.01); *A61B 2018/00994* (2013.01); *F21W 2131/20* (2013.01)

(58) Field of Classification Search
CPC . A61B 2018/00982; A61B 2018/00994; F21S 10/06; F21W 2131/20
USPC .......................................................... 606/4, 6
See application file for complete search history.

(56) References Cited

U.S. PATENT DOCUMENTS

| | | | | |
|---|---|---|---|---|
| 10,939,815 | B2* | 3/2021 | LaBelle | A61B 3/0008 |
| 2011/0230728 | A1 | 9/2011 | Artsyukhovich et al. | |
| 2014/0180264 | A1* | 6/2014 | Diao | A61F 9/00821 |
| | | | | 606/4 |
| 2016/0120699 | A1* | 5/2016 | Farley | A61F 9/00736 |
| | | | | 606/4 |
| 2016/0174834 | A1* | 6/2016 | Eslami | A61B 8/485 |
| | | | | 351/246 |
| 2016/0175149 | A1* | 6/2016 | McDonell | A61F 9/00745 |
| | | | | 600/249 |
| 2017/0165114 | A1* | 6/2017 | Hallen | A61F 9/00736 |
| 2017/0172792 | A1* | 6/2017 | Mirsepassi | A61B 3/0008 |
| 2018/0078315 | A1* | 3/2018 | Ren | A61F 9/007 |
| 2018/0147087 | A1* | 5/2018 | Bacher | A61B 3/0008 |
| 2021/0038070 | A1* | 2/2021 | Charles | A61B 3/14 |
| 2021/0145642 | A1* | 5/2021 | Berlin | G06N 20/00 |
| 2023/0165714 | A1* | 6/2023 | Hallen | A61F 9/00825 |
| | | | | 606/6 |
| 2023/0181025 | A1* | 6/2023 | Hallen | A61B 90/30 |
| | | | | 600/249 |
| 2023/0346600 | A1* | 11/2023 | Hallen | A61F 9/00825 |

\* cited by examiner

OPHTHALMIC SURGICAL MICROSCOPE WITH STROBOSCOPIC ILLUMINATION

TECHNICAL FIELD

The present disclosure relates generally to methods and systems for visualization of interactions within or associated with an ocular space of an eye.

BACKGROUND

During small incision surgery, and particularly during ophthalmic surgery, small probes are inserted into the operative site to break-down, remove, or otherwise manipulate tissue. During these surgical procedures, fluid and tissue may be broken-down (e.g., cut or emulsified), and/or removed from the surgical site. Visualization of the procedures is difficult due to the high frequency and/or power utilized in manipulating the tissue.

Examples of ophthalmic surgeries during which fluid and tissue are broken-down, removed, or otherwise manipulated include vitreo-retinal procedures. Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, CMV retinitis, and many other ophthalmic conditions. In order to treat certain conditions in the back of the eye, a surgeon may first perform vitrectomy, as part of the vitreo-retinal procedure that is being performed. Vitrectomy refers to a surgical removal of the vitreous, which is a normally clear, gel-like substance that fills the center of the eye. The vitreous may make up approximately two-thirds of the eye's volume, giving it form and shape before birth.

Removal of vitreous can involve a vitrector (also referred to as the "cutter" or "vitreous cutter"). In some examples, the vitrector may be powered by a pneumatic vitrectomy machine (e.g., surgical console) including one or more pneumatic valves (also referred to as drive valves). In such examples, the vitrector may work like a tiny guillotine, with an oscillating microscopic cutter to remove the vitreous gel in a controlled fashion. In some other examples, the vitrector may cut the vitreous using laser light or some other technology such as ultrasound. In addition to cutting the vitreous, the cutter may also be configured to remove or aspirate the surgically cut vitreous.

Other examples of ophthalmic surgeries during which fluid and tissue are cut, removed, or otherwise manipulated include phacoemulsification, which refers to a cataract operation in which a diseased lens is emulsified and aspirated out of the lens capsule. In some examples, the phacoemulsification probe may emulsify the lens by ultrasound (or other technologies, such as laser light, etc.).

Thus, probes utilized in ophthalmic surgeries interact with and/or manipulate ocular matter through a variety of means, such as oscillating microscopic cutters, laser light, ultrasound, and vacuum aspiration. A surgeon may visualize the ocular interactions with the aid of a microscope. The microscope may provide an illumination source, such as an LED, to illuminate the operating area. In addition to, or in lieu of, the microscope's illumination source, an illumination probe may be inserted into the eye to illuminate the ocular space. The surgeon may then react to the visual feedback. For example, if the probe appears to be approaching a sensitive region of the eye, the surgeon may react by changing the direction or orientation of the probe, changing the energy characteristics of the probe, and/or retracting the probe. However, modern probes often operate at high frequencies and/or with high power. Often, the interactions of the probe with the ocular matter happen too quickly for the surgeon to visually detect and/or to react in time to prevent causing damage to the eye. It would be beneficial for surgeons to have available tools for visualizing ophthalmic surgical interactions with high time precision.

BRIEF SUMMARY

The present disclosure relates generally to methods and systems for visualization of interactions within or associated with an ocular space of an eye.

Certain embodiments provide an ophthalmic system for visualization of interactions between ocular matter and a probe tip of a probe within or in contact with an ocular space of an eye. The system comprises: a visualization tool having a field of view that includes at least a portion of the ocular space of the eye where the probe tip interfaces with the ocular matter; and a stroboscopic illumination source configured to stroboscopically illuminate at least the portion of the field of view at an illumination frequency.

Certain embodiments provide a method of operating a stroboscopic illumination source during an ophthalmic surgical procedure. The method comprises: identifying an illumination source type of the stroboscopic illumination source, wherein the stroboscopic illumination source is configured to stroboscopically illuminate at least a portion of a field of view of a visualization tool at an illumination frequency; identifying a probe type of a probe used for the ophthalmic surgical procedure, the probe having a probe tip that is configured to contact ocular matter in the portion of the field of view of the visualization tool; identifying a first procedure trigger corresponding to a first operation of the ophthalmic surgical procedure; and operating the stroboscopic illumination source based on the probe type, the illumination source type, and the first procedure trigger.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
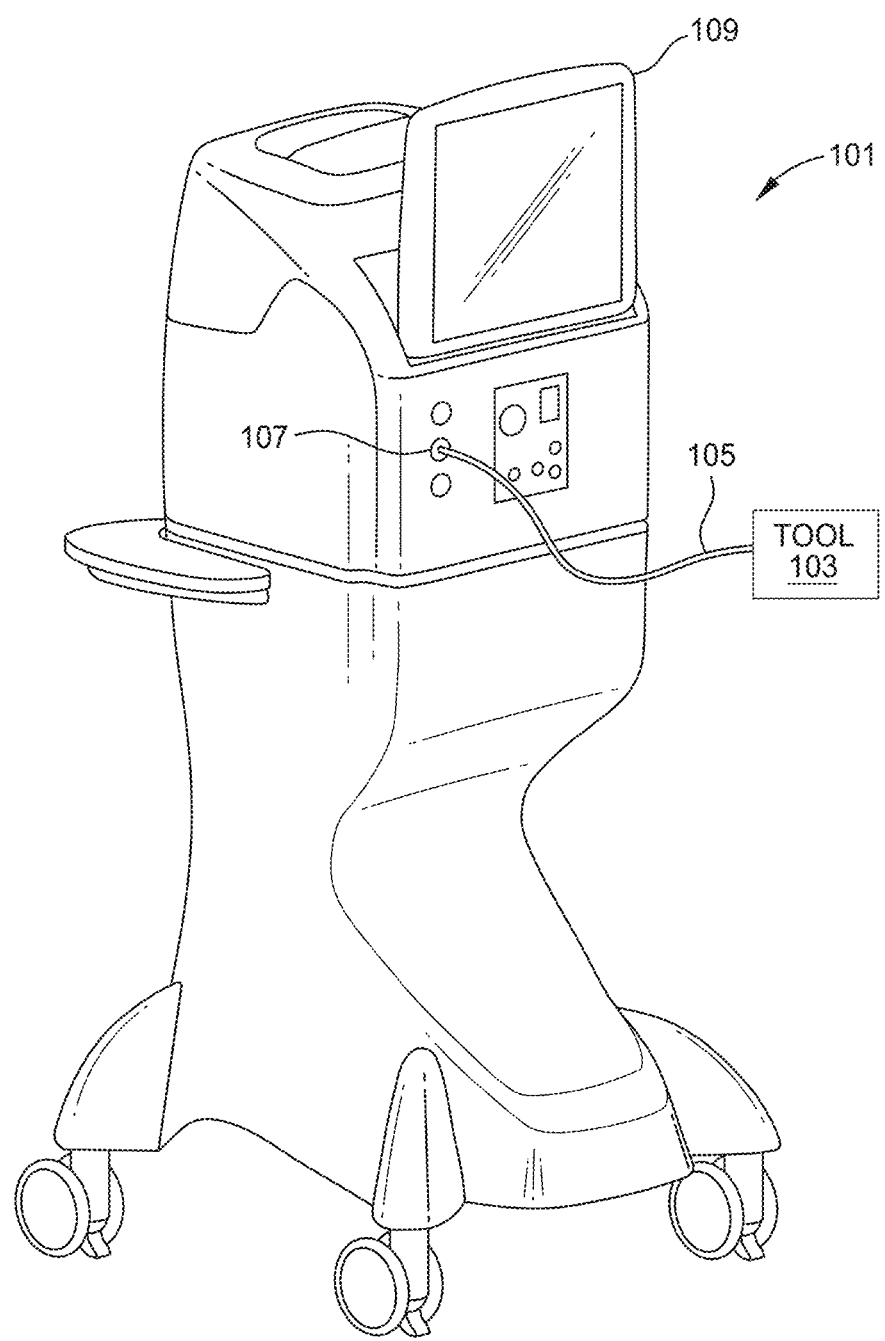
FIG. 1 illustrates an example surgical console, in accordance with certain embodiments.

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Embodiments include devices and methods related to ophthalmic surgical visualization tools with stroboscopic illumination. Often, interactions of a surgical probe with ocular matter happen too quickly for the surgeon to visually detect and/or to react in time to prevent causing damage to the eye. Therefore, it may be beneficial to utilize ophthalmic surgical visualization tools with stroboscopic illumination to illuminate a surgical site such that details of ocular interactions may be visualized.

As used herein, the phrase "ocular space" generally refers to intraocular spaces, extraocular spaces (e.g., ocular surfaces, such as the surface of the cornea), and periocular spaces (e.g., spaces surrounding the eye, such as interfaces between the eyelid and the eye). Similarly, the phrase "ocular matter" generally refers to intraocular matter, extraocular matter (e.g., a cornea surface), and periocular matter (e.g., matter associated with interfaces between the eyelid and the eye, such as the Schlemm's canal, the lacrimal gland, and the nasolacrimal duct).

Ophthalmic surgical visualization tools with stroboscopic illumination may be utilized to illuminate details of ocular interactions, such as a location of a surgical probe relative to ocular structures (e.g., retina, lens capsule, etc.), breaking-off and/or movement of vitreous during vitrectomy, breaking-off and/or movement of lens particles in response to phacoemulsification, cavitation bubbles, gas propagation, ablation plumes, etc. Stroboscopic illumination allows visualization of fast (e.g., high speed, high frequency, or high power) processes by converting the view from a continuous, high-speed image into a discontinuous, slowed-down appearance. Stroboscopic illumination may improve visualization, whether with a "naked eye", lens-assisted visualization (e.g., with a microscope), or with a video camera. It may be said that the stroboscopic illumination "slows down" the visual details of the ocular interaction. The surgeon may utilize stroboscopic illumination to improve visualization and thus better identify when and how to utilize a probe during an ophthalmic surgical procedure. Thus, stroboscopic illumination can reduce risk and improve the quality of the surgery. For example, stroboscopic illumination can increase the safety of surgery near to the retina and/or the capsular bag.

FIG. 1 illustrates an example of a surgical console 101, according to certain embodiments. Surgical console 101 may be configured to drive one or more tools 103, which may include ophthalmic probes of a variety of probe types, including laser probes (e.g., picosecond infrared laser probes, femtosecond laser probes), vitrectomy probes, phacoemulsification probes, flap cutters, and other ophthalmic surgical tools. In operation, surgical console 101 may function to assist a surgeon in performing various ophthalmic surgical procedures, such as vitrectomy, phacoemulsification, cataract surgery, LASIK, and similar procedures.

In embodiments where tool 103 is a vitrector, surgical console 101 may include one or more modules or components to power the vitrector for the purpose of breaking-down (e.g., cutting) the vitreous. For example, in certain embodiments, surgical console 101 may include a pneumatic module that uses compressed gas, such as nitrogen, to power the vitrector. In certain other embodiments, surgical console 101 may include a laser source for generating laser light that is used by the vitrector to break-down the vitreous (for example, see US Patent Publication 2019/0201238).

In some embodiments, tool 103 may be a phacoemulsification probe. For example, tool 103 may be an ultrasonic phacoemulsification probe that is capable of emulsifying or breaking-down a lens during cataract surgery. As another example, tool 103 may be configured to emit laser light for lens emulsification. In embodiments where tool 103 is a phacoemulsification probe, surgical console 101 includes one or more modules or components to power the phacoemulsification probe to emulsify the lens during cataract surgery. In some embodiments, tool 103 may be a picosecond infrared laser (pIRL).

In some embodiments, tool 103 may be configured to emit laser light, such as femtosecond laser light, used to make incisions and/or cut flaps during ophthalmic surgery. A suitable example femtosecond laser is a WaveLight® F S200 laser available from Alcon of Fort Worth, Texas. In some embodiments, tool 103 may be a laser, for example an excimer laser for photorefractive keratectomy and/or LASIK procedures (e.g., laser ablation of the cornea). A suitable example excimer laser is a WaveLight® EX500 laser available from Alcon of Fort Worth, Texas.

The surgical console 101 may include a display 109 for displaying information to a user (the display may also incorporate a touchscreen for receiving user input). Tool 103 is operatively coupled to the surgical console 101 through a line 105 that connects to port 107. Note that line 105 may be representative of a number of tubes that may couple tool 103 with surgical console 101. For example, line 105 may be representative of a pneumatic line, an optical fiber cable, or an ultrasound power line for powering tool 103 for cutting purposes as well as an aspiration or vacuum line for transporting the aspirated matter back to surgical console 101.

Figure 2:
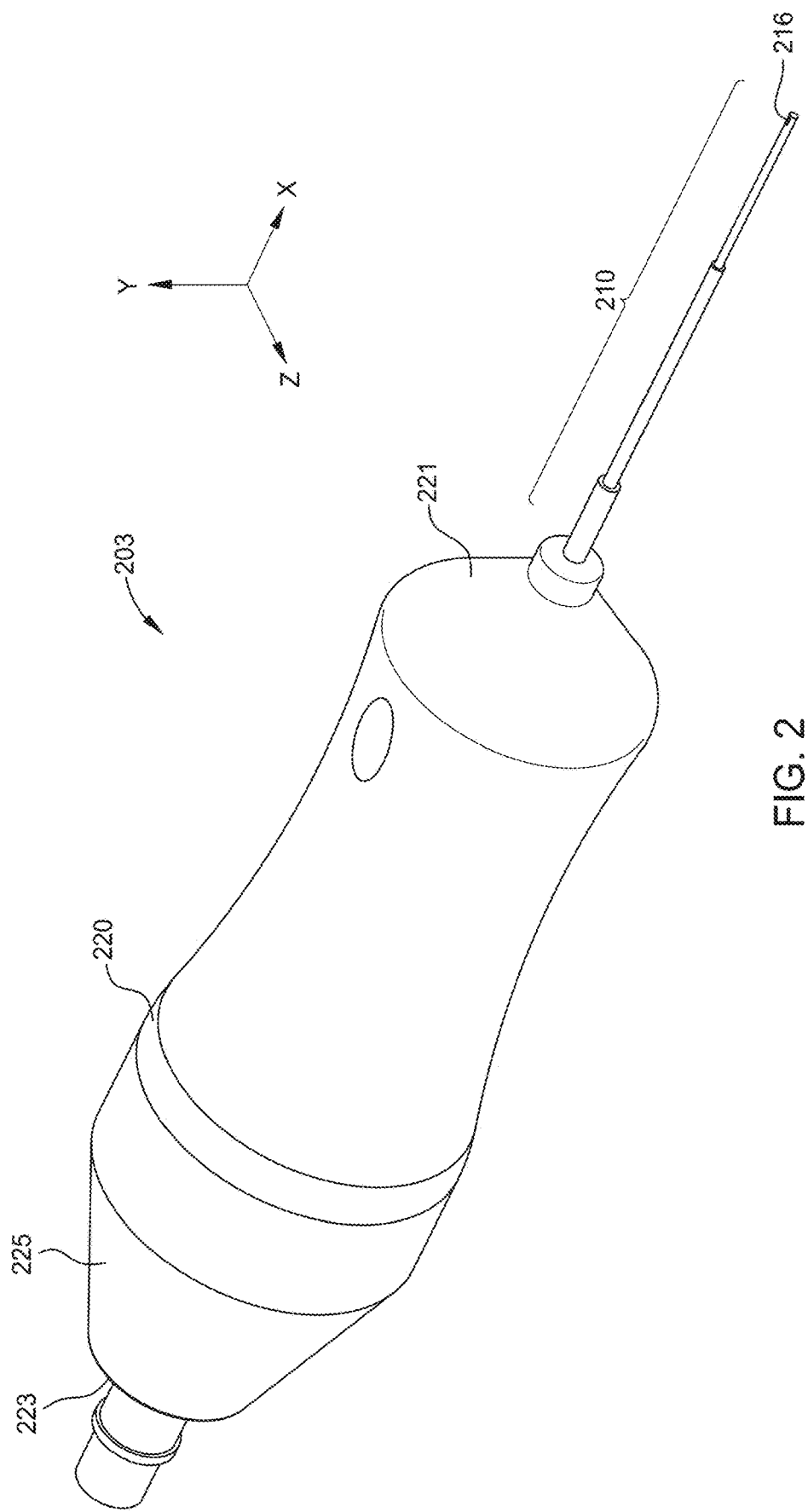
FIG. 2 illustrates an example vitrectomy probe, in accordance with certain embodiments.

FIG. 2 illustrates a perspective view of an exemplary vitrector 203, according to certain embodiments described herein. Vitrector 203 is an example of tool 103. As depicted in FIG. 2, vitrector 203 comprises a probe 210 and a base unit 220. Probe 210 is partially and longitudinally disposed through a distal end 221 of base unit 220 and may be directly or indirectly attached thereto within an interior chamber of base unit 220. Probe 210 may be inserted into an eye for performing vitrectomy. Note that, as described herein, a distal end or portion of a component refers to the end or the portion that is closer to a patient's body during use thereof. On the other hand, a proximal end or portion of the component refers to the end or the portion that is distanced further away from the patient's body.

Base unit 220 further provides a port 223 at a proximal end 225 thereof for one or more supply lines to be routed into an interior chamber of the base unit 220. In certain embodiments, port 223 may be representative of two or more ports. In certain embodiments, port 223 may provide a connection between the base unit 220 and a tube or vacuum line (e.g., line 105 of FIG. 1) of a vacuum generator (e.g., a vacuum generator in surgical console 101) for aspiration. In certain embodiments, port 223 may provide a connection to an optical fiber cable that couples to one or more laser light sources (e.g., in surgical console 101) for providing laser light that is used by vitrector 203 for cutting the vitreous. In certain embodiments, port 223 may provide a connection to pneumatic line that that couples a pneumatic module (e.g., in surgical console 101) that uses compressed gas, such as nitrogen, to power vitrector 203 for cutting the vitreous. Note that the vitrector 203 may be powered using other technologies, as one of ordinary skill in the art appreciates. Vitrector 203 comprises a cutting port at the tip 216 (i.e., distal portion) of probe 210. In certain embodiments, vitrector 203 is able to cut and aspirate the vitreous through this port.

Note that FIG. 2 illustrates only one example of a vitrector. As described above, laser light or other mechanism may instead be used. For example, vitrector 203 may include a probe 210 that emanates laser light from the tip 216 of the probe 210, in lieu of the cutting port.

Figure 3:
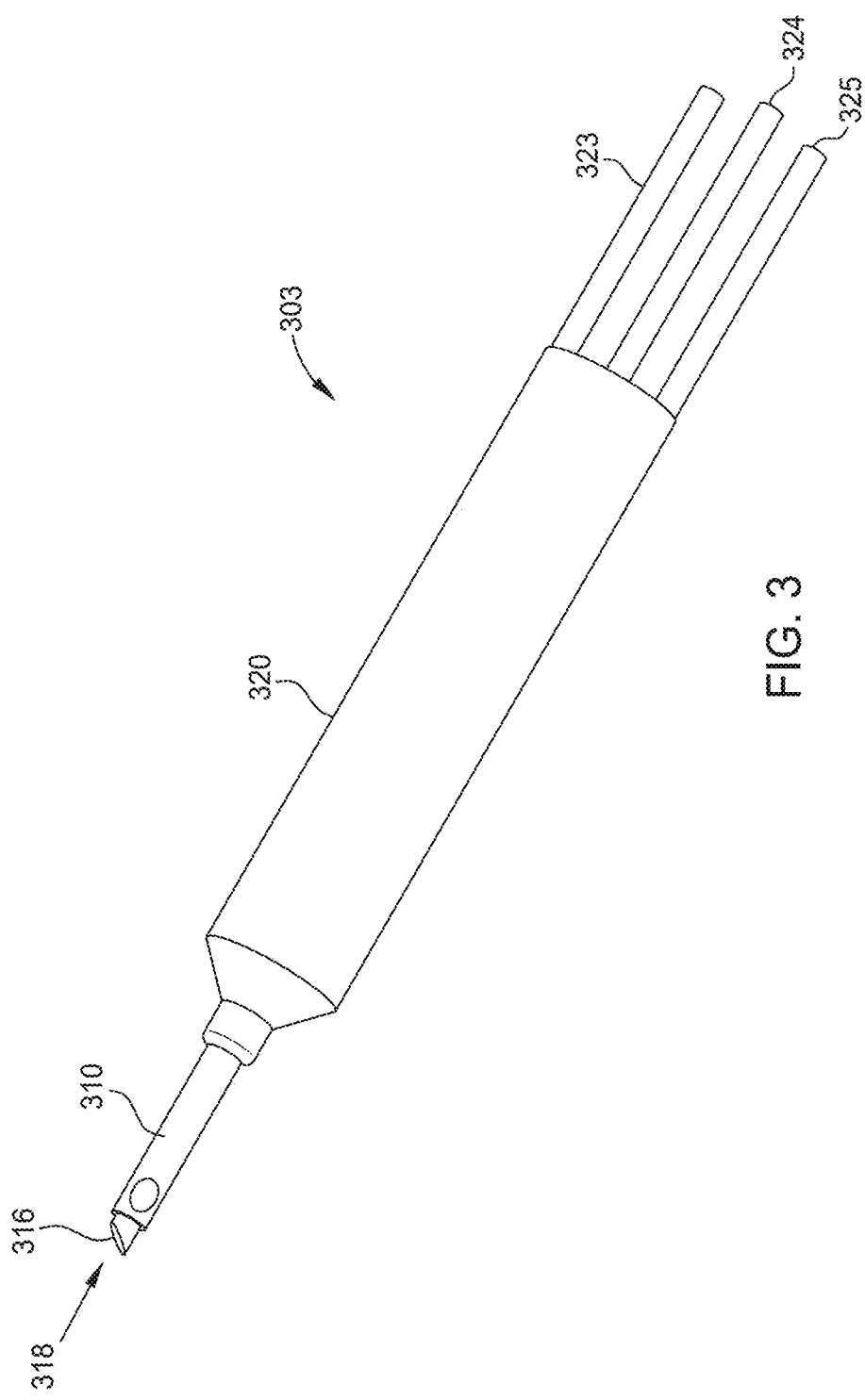
FIG. 3 illustrates an example phacoemulsification probe, in accordance with certain embodiments.

FIG. 3 illustrates a perspective view of an exemplary phacoemulsification probe 303, according to certain embodiments described herein. Phacoemulsification probe 303 is another example of tool 103. As depicted in FIG. 3, phacoemulsification probe 303 comprises a handpiece body 320 and probe 310 that may be inserted into an eye for performing phacoemulsification. An emulsification tip 316 extends beyond the distal end of probe 310. Emulsification tip 316 is a hollow cylindrical tube or shaft that propagates ultrasound waves provided by an ultrasound power line 324. The ultrasound waves are capable of breaking-down (e.g., emulsifying) the lens. Emulsification tip 316 also provides an aspiration port 318 through which the emulsified lens is aspirated as a result of the vacuum pressure provided by an aspiration line 323. Tool 303 also has an irrigation port for irrigating the lens during the phacoemulsification process through an irrigation line 325. Note that FIG. 3 illustrates only one example of a phacoemulsification probe. Also, FIG. 3 only illustrates one example of an emulsification mechanism that may be used as part of a phacoemulsification probe.

As described above, the use of stroboscopic illumination during various ophthalmic surgical procedures improves a surgeon's visualization of the interactions between a surgical probe and ocular matter and, thus, allows the surgeon to more effectively adjust the position of and/or use the surgical probe inside of the eye. For example, while operating the surgical probe, the use of stroboscopic illumination may help the surgeon visually detect or identify the real-time location of the surgical probe's tip inside the eye and, in certain situation, react in time to prevent causing damage to the eye. Accordingly, the embodiments herein describe a variety of different systems and techniques for using stroboscopic illumination.

Figure 4A:
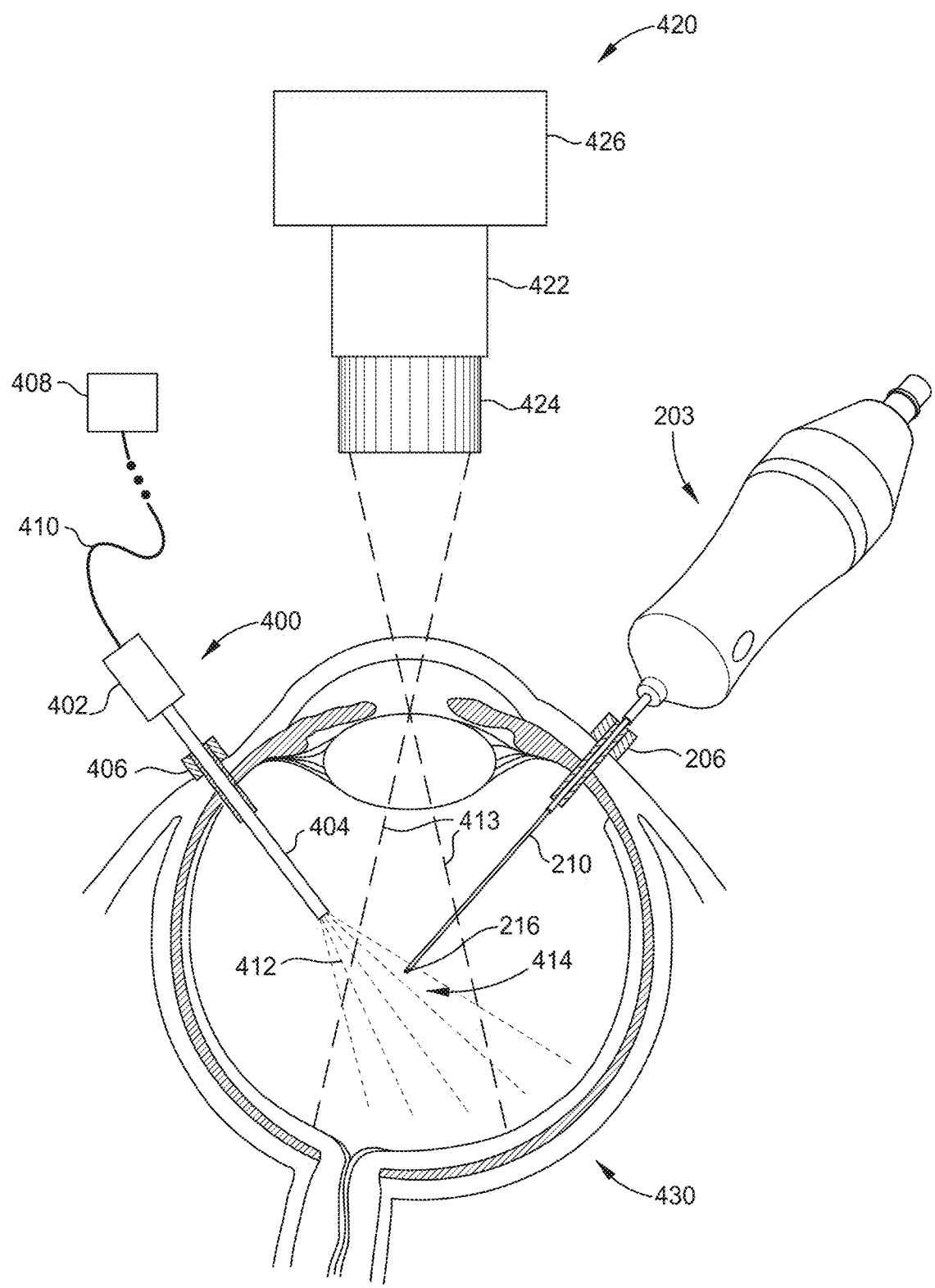
FIG. 4A illustrates a cross-sectional view of an eye during an exemplary ophthalmic surgical procedure utilizing the example vitrectomy probe of FIG. 2 with endo-illuminator stroboscopic illumination, in accordance with certain embodiments.
Figure 4B:
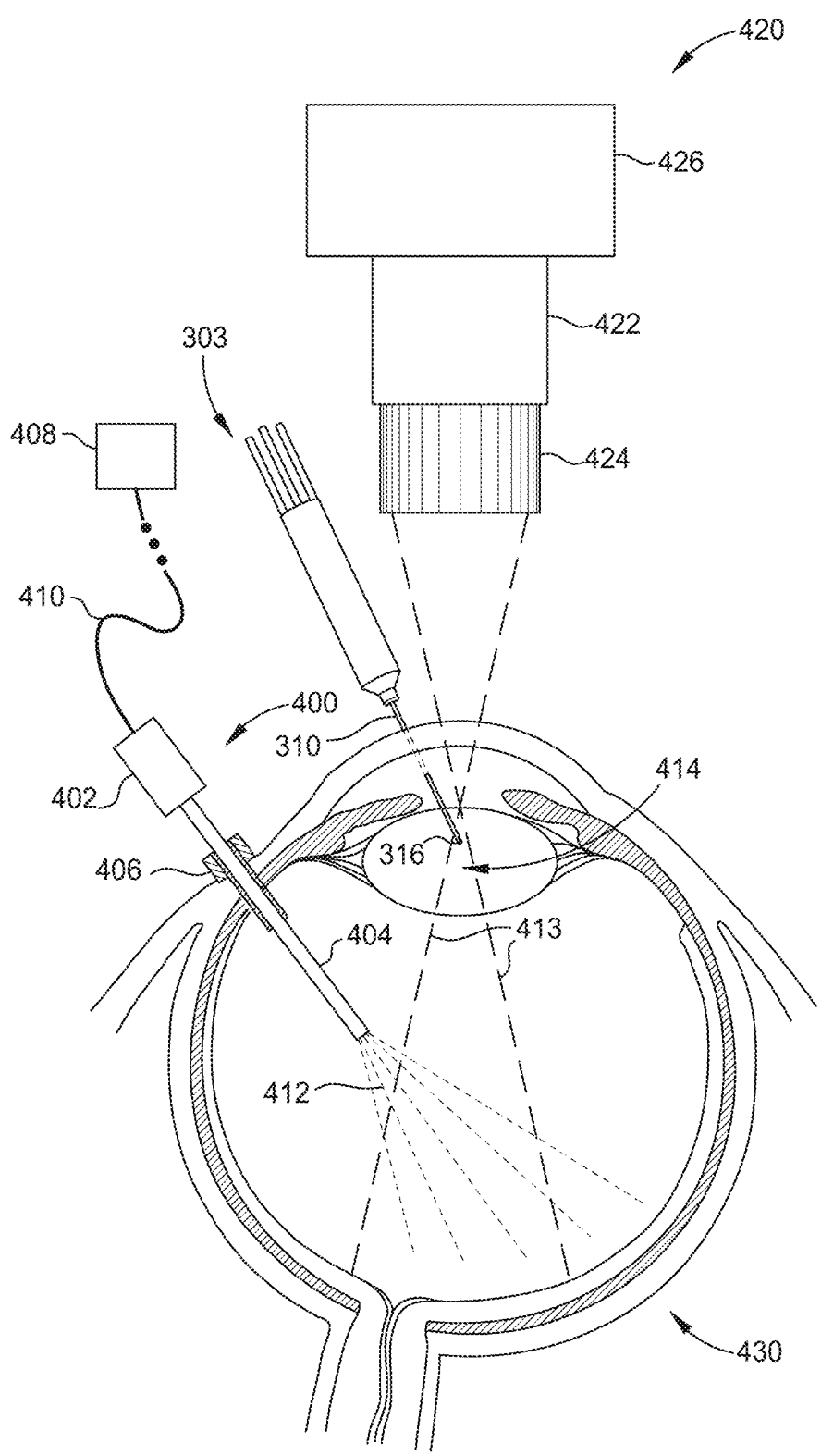
FIG. 4B illustrates a cross-sectional view of an eye during an exemplary ophthalmic surgical procedure utilizing the example phacoemulsification probe of FIG. 3 with endo-illuminator stroboscopic illumination, in accordance with certain embodiments.
Figure 5A:
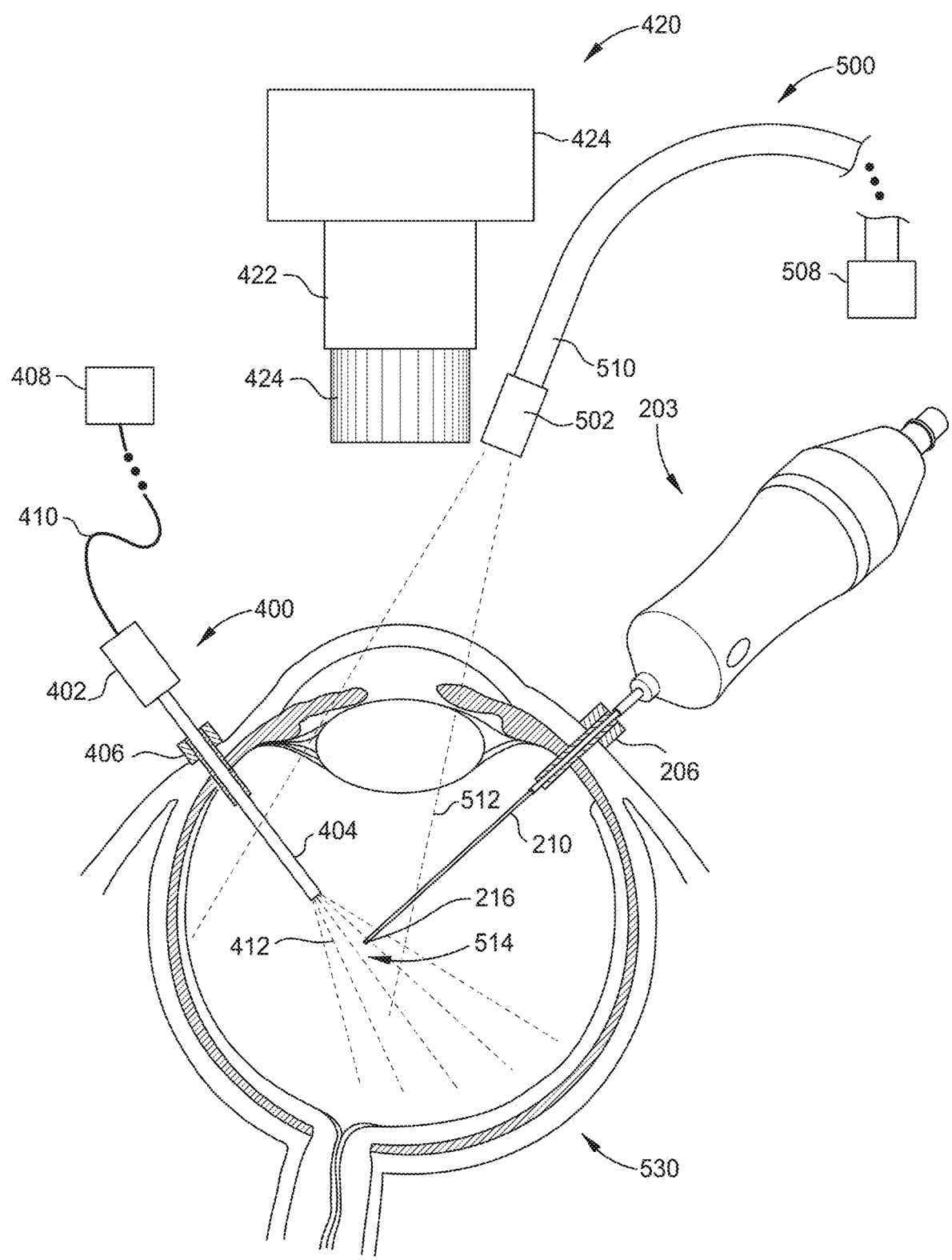
FIG. 5A illustrates a cross-sectional view of an eye during an exemplary ophthalmic surgical procedure utilizing the example vitrectomy probe of FIG. 2 with external stroboscopic illumination, in accordance with certain embodiments.
Figure 5B:
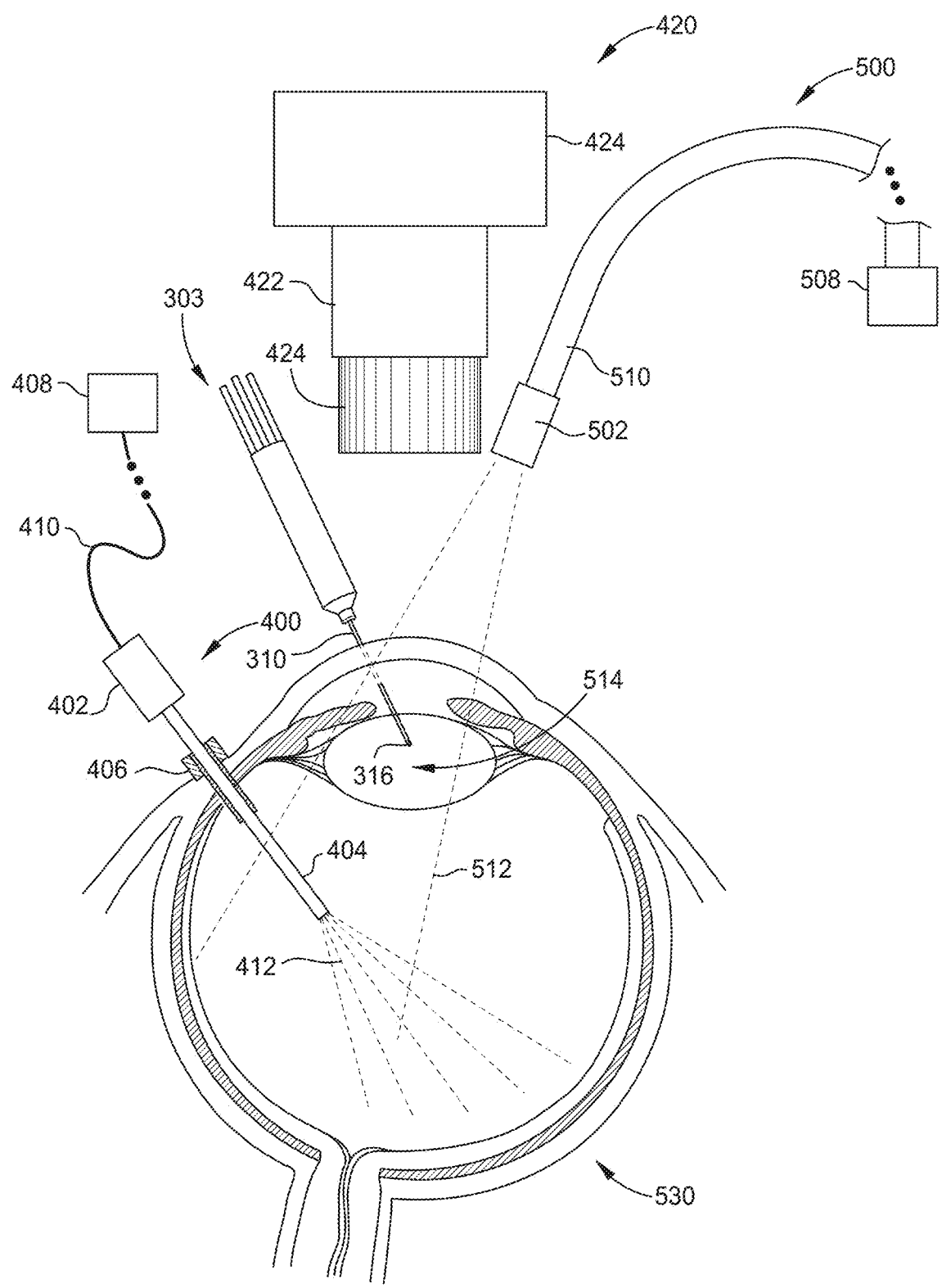
FIG. 5B illustrates a cross-sectional view of an eye during an exemplary ophthalmic surgical procedure utilizing the example phacoemulsification probe of FIG. 3 with external stroboscopic illumination, in accordance with certain embodiments.
Figure 6A:
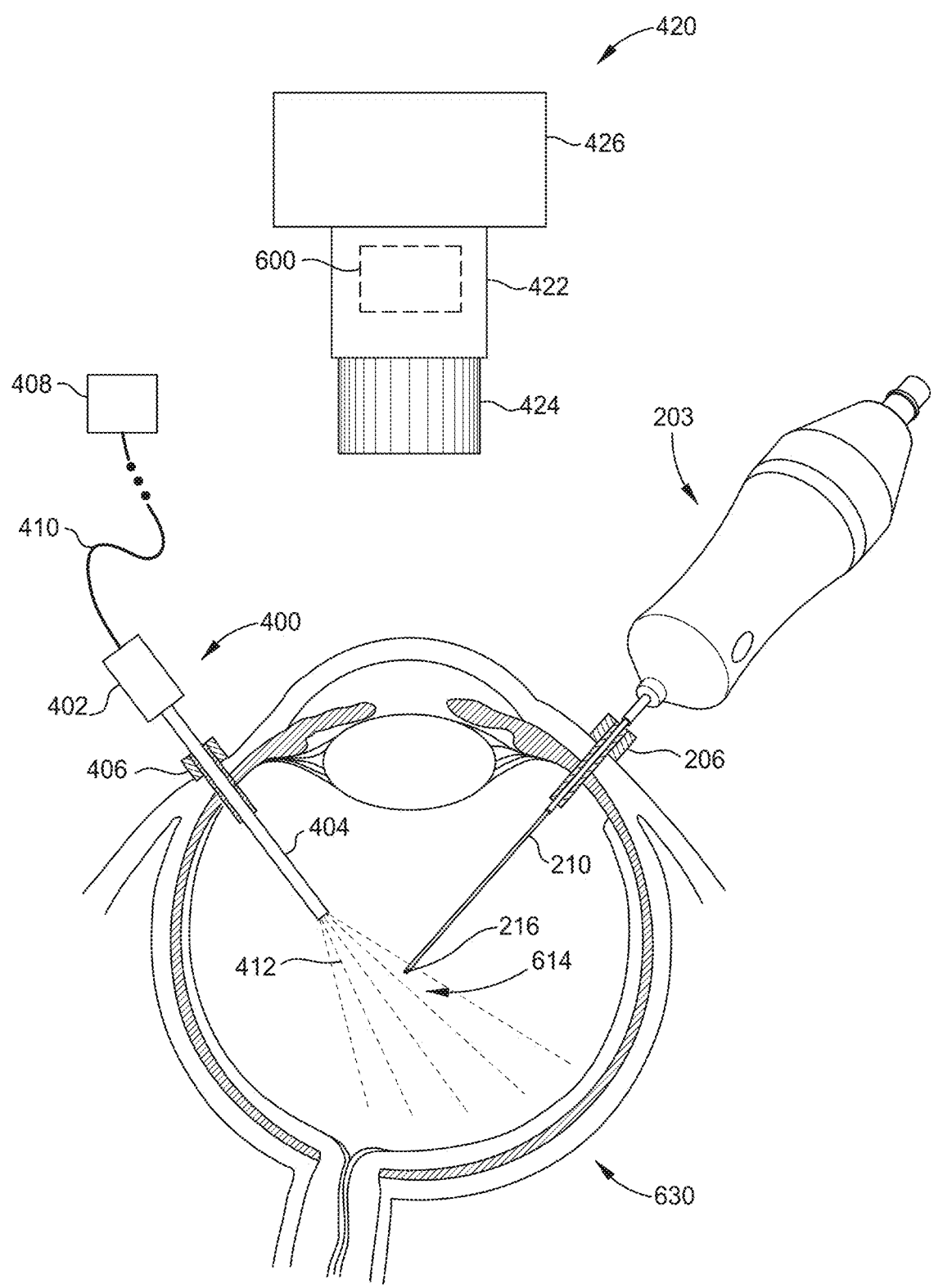
FIG. 6A illustrates a cross-sectional view of an eye during another exemplary ophthalmic surgical procedure utilizing the example vitrectomy probe of FIG. 2 with external stroboscopic illumination, in accordance with certain embodiments.
Figure 6B:
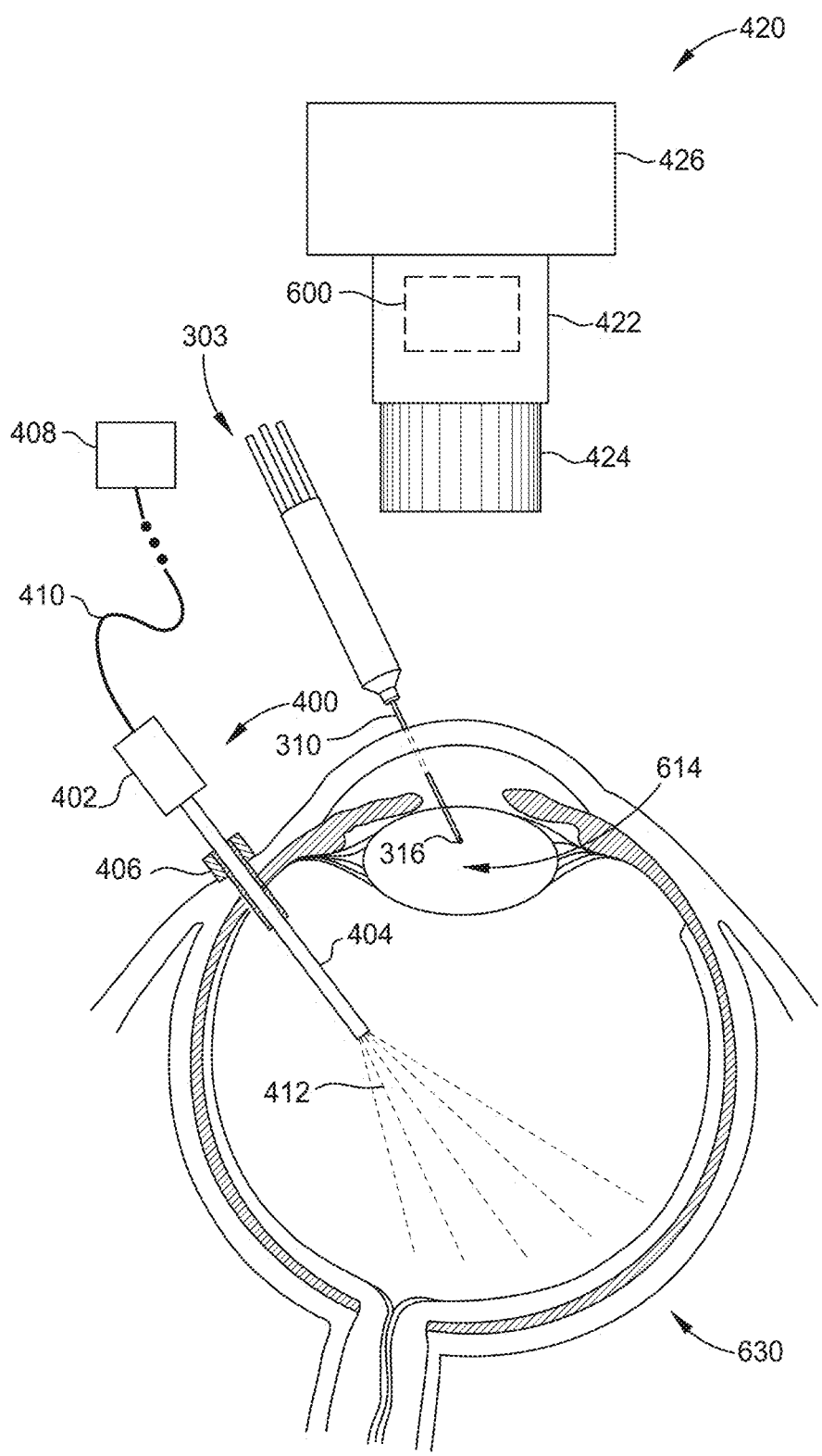
FIG. 6B illustrates a cross-sectional view of an eye during another exemplary ophthalmic surgical procedure utilizing the example phacoemulsification probe of FIG. 3 with external stroboscopic illumination, in accordance with certain embodiments.
Figure 7A:
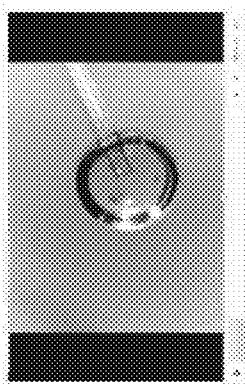
FIGS. 7A-7L illustrate an exemplary stroboscopic visualization of an interaction between energy emitted from the tip of a probe and surrounding fluid, in accordance with certain embodiments.
Figure 7B:
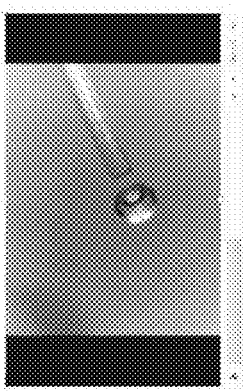
Figure 7C:
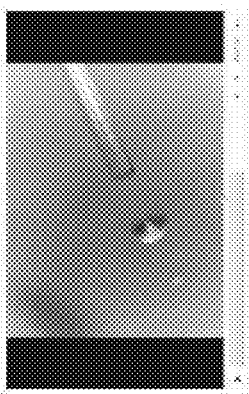
Figure 7D:
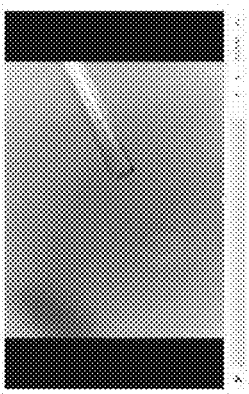
Figure 7E:
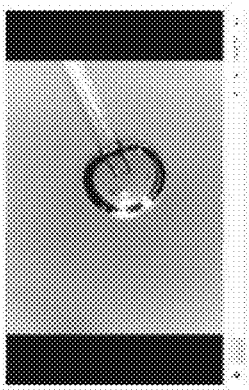
Figure 7F:
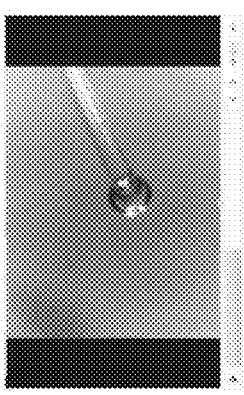
Figure 7G:
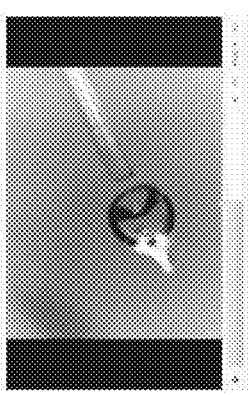
Figure 7H:
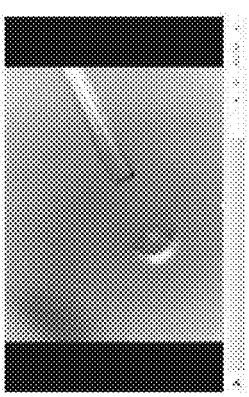
Figure 7I:
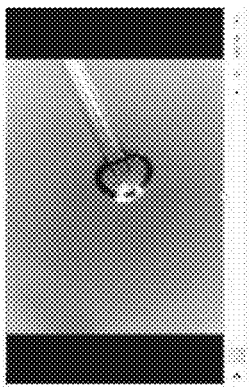
Figure 7J:
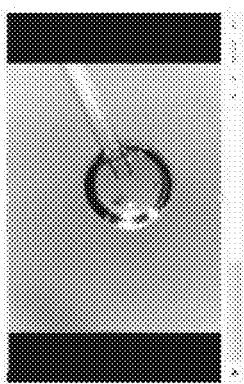
Figure 7K:
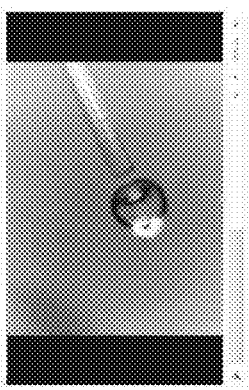
Figure 7L:
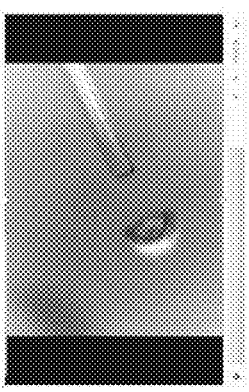

In the embodiments of FIGS. 4A and 4B, described under the heading "Endo-illuminator Stroboscopic Illumination," stroboscopic illumination is provided by an endo-illumination device. In the embodiments of FIGS. 5A and 5B, described under the heading "External Stroboscopic Illumination," stroboscopic illumination is provided by an external illumination device (i.e., an illumination device situated outside of the eye during the surgical operation). In the embodiments of FIGS. 6A and 6B, described under the heading "Microscopy Stroboscopic Illuminator," stroboscopic illumination is provided by a microscopy illuminator that is an integral part of a visualization tool. Note that the various embodiments described with reference to FIGS. 4A-4B, 5A-5B, and 6A-6B may include one or more sources of continuous illumination in addition to at least one source of stroboscopic illumination.

Also note that FIGS. 4A, 5A, and 6A are provided to illustrate that stroboscopic illumination can be advantageously used during vitrectomy procedures involving a vitrector, similar to vitrector 203. FIGS. 4B, 5B, and 6B are provided to illustrate that stroboscopic illumination can be advantageously used while phacoemulsification is performed using phacoemulsification probe, similar to phacoemulsification probe 303. Finally, note that although FIGS. 4A-4B, 5A-5B, and 6A-6B illustrate the usage of stroboscopic illumination with respect to a vitrector 203 and a phacoemulsification probe 303, the embodiments described herein are applicable any other type of ophthalmic procedure, involving different types of surgical probes, examples of which were previously discussed.

Endo-Illuminator Stroboscopic Illumination

FIGS. 4A and 4B illustrate a cross-sectional view of an eye 430 during exemplary ophthalmic surgical procedures utilizing a surgical probe (e.g., tool 103) with an endo-illuminator stroboscopic illumination. As illustrated in FIG. 4A, a vitrector 203 and an endo-illumination device 400 are inserted into an ocular space of eye 430. The endo-illumination device 400 illuminates at least the ocular space near the tip 216 of probe 210 of vitrector 203 for viewing with a visualization tool 420 (e.g., a microscopy system). As further described below, a surgical console, such as surgical console 101, may receive information from, deliver instructions to, and/or otherwise communicate with one or more of the vitrector 203, the light source 408, and the visualization tool 420.

As illustrated in FIG. 4A, visualization tool 420 provides visualization of a portion of the interior of eye 430, as indicated by dashed lines 413 demarking field of view 414.

The light 412 emitted from endo-illumination device 400 illuminates at least a portion of the field of view 414, thereby allowing that portion, and possibly additional portions of the interior of the eye 430, to be viewed with visualization tool 420. The visualization tool 420 may include any microscope suitable for ophthalmic surgery, including an operating microscope or a digital visualization system (e.g., digital microscope). In the example shown, the visualization tool 420 includes a body 426, an objective 422, and an attachment 424 (e.g., a polarization filter, a coaxial light source, etc.).

In some embodiments, visualization tool 420 includes (e.g., internally integrated, externally attached, etc.) a microscopy illuminator (not shown). For example, the microscopy illuminator can be located proximally with respect to objective 422 or any other suitable location, as one of ordinary skill in the art appreciates. Note that in embodiments where the microscopy illuminator is located proximally with respect to objective 422, the optical axis of objective 422 (also referred to herein as "visualization axis" of visualization tool 420) may be parallel or coaxial with respect to the illumination axis of the microscopy illuminator.

In embodiments of FIG. 4A, the microscopy illuminator may provide continuous illumination (e.g., bright, background, broad-wavelength band, narrow-wavelength band, and/or white light) to illuminate the surgical field. The microscopy illuminator can include an incandescent light bulb, a halogen light bulb, a metal halide light bulb, a xenon light bulb, a mercury vapor light bulb, a light-emitting diode (LED), a fluorescent light, other suitable components, and/or combinations thereof that provide continuous light. In some embodiments, the operations of the microscopy illuminator may be controlled by surgical console 101. For example, the surgical console 101 may transmit control signals to the microscopy illuminator to switch the microscopy illuminator on or off or alter its voltage, wavelength, etc.

As illustrated in FIG. 4A, the endo-illumination device 400 includes a handpiece 402 coupled to the proximal end of a shaft or "tube" 404. The handpiece 402 is removably coupled to a distal end of an optical cable 410 having a proximal end coupled to a light source 408. Light source 408 may include a light-emitting diode (LED), a broadband laser source, or other source of light suitable for ophthalmic surgery. In certain embodiments, the light source 408 is an integral part of surgical console 101, which also controls vitrector 203. In certain other embodiments, the light source 408 is an independent unit. In such embodiments, as described in further detail below, the light source 408 may be communicatively coupled to (e.g., wired or wirelessly) surgical console 101

Regardless of whether or not light source 408 is an integral part of surgical console 101, in certain embodiments, the surgical console 101 may control the operations of light source 408. Controlling the operations of light source 408 includes controlling the frequency with which light source 408 provides stereoscopic illumination for illuminating the field of view 414 through endo-illumination device 400. Controlling the frequency of the light source 408 may include synchronizing the frequency of the light source 408 with a driving frequency with which the vitrector 203 is operated at least during certain procedures of a vitrectomy operation. Controlling the operations of light source 408 may also include sending control signals to light source 408 to cause it to switch from providing stroboscopic illumination to providing continuous illumination and vice versa.

The handpiece 402 is configured to provide a user (e.g., an ophthalmic surgeon) with a graspable portion of the endo-illumination device 400 to provide the surgeon a means for manipulating the depth and location of the tube 404 within the eye 430, and for directing the emitted light 412. Tube 404 is a substantially hollow stainless steel shaft or hypodermic tubing, configured to be inserted into the eye 430 via an insertion cannula 406. Note that, although shown and referred to as an endo-illumination device, the endo-illumination device 400 may include any of a variety of illumination probes, including an ophthalmic chandelier probe or another suitable surgical illumination devices.

The endo-illumination device 400 is further configured to house one or more optical fibers configured to direct light out of a distal end of the tube 404. For example, the optical fibers may include a single optical fiber, an optical fiber array (e.g., a plurality of optical fibers in regular linear arrangement or 2-dimensional pattern arrangement) and/or a multi-core optical fiber (e.g., a single-mode (SM) or multi-mode (MM) fiber with multiple cores). In particular, the hollow portion of the tube 404 includes an interior compartment configured to house the optical fiber(s). It should be noted that, in some embodiments, light source 408 is not external to the handpiece 402. For example, in certain embodiments, the handpiece 402 contains light source 408 within a housing or structure of the handpiece 402.

In certain embodiments of FIG. 4A, the endo-illumination device 400 illuminates the portion of field of view 414 with stroboscopic light at least during certain procedures during the surgical operation performed using vitrector 203. More specifically, the endo-illumination device 400 may illuminate the surgical field with pulses of light (e.g., broad-wavelength band light, narrow-wavelength band light) with a certain illumination frequency.

In some embodiments, one or more of the microscopy illuminator and the endo-illumination device 400 may provide polarized light. Flow fields are known to induce flow birefringence therefore polarized stroboscopic illumination may be utilized to visualize the flow field around the tip of the surgical probe (e.g., tip of vitrector 203 or the phacoemulsification probe 303, etc.). In some embodiments, the optical fibers of endo-illumination device 400 may include one or more of a polarization maintaining fiber, a polarizing fiber, and/or any other fiber suitable for transmission of light. The polarization maintaining fiber may maintain an existing polarization direction that is aligned with a birefringence axis of the fiber, and is capable of maintaining a polarization direction. Similarly, an optical fiber can be stressed (e.g., lateral pressure on the wire) to induce a birefringence axis in order to maintain the polarization of light passed through the fiber. In contrast, a polarizing fiber may receive polarized or unpolarized light, and propagate the light in one polarization direction while preventing propagation of the light in all other directions. For example, the polarizing fiber may receive transmitted light and filter an incident component (i.e., prevent emission of the incident component of light by reflection or absorption) while emitting a polarized component of the transmitted light.

Accordingly, polarizing fibers can polarize, maintain polarization, and/or change direction of already polarized light being propagated through the fibers. For example, in some embodiments, the light source 408 drives unpolarized light into the entry-point of the optical cable 410, which provides the light to the optical fibers of the endo-illumination device 400. In such embodiments, the endo-illumination device 400 may be configured to polarize the unpolarized light. In some embodiments, the light source 408 drives linearly, circularly, or elliptically polarized light into the optical cable 410. In such embodiments, the optical cable 410 and/or the endo-illumination device 400 may include polarization maintaining optical fibers configured to maintain the polarization direction of the light in the optical cable 410. Also, in some embodiments, the endo-illumination device 400 may be configured to change the polarization of the received polarized light.

Similar to FIG. 4A, FIG. 4B illustrates a cross-sectional view of an eye 430 during another exemplary ophthalmic surgical procedure utilizing endo-illuminator stroboscopic illumination. As illustrated in FIG. 4B, phacoemulsification probe 303 is inserted into the lens capsule of eye 430. Similar to FIG. 4A, endo-illumination device 400 illuminates the ocular space of the eye 430 using stroboscopic illumination, at least during certain procedures of the surgical operation performed using the phacoemulsification probe 303. The light from endo-illumination device 400 may reflect off of the retina to backward-illuminate the lens space for viewing with visualization tool 420. Note that endo-illumination device 400, light source 408, visualization tool 420, and surgical console 101 all operate in a manner similar to what was described with respect to FIG. 4A.

As described above, although endo-illumination device 400 is capable of providing stroboscopic illumination, in certain embodiments, the endo-illumination device 400 may switch to providing continuous light for illuminating at least the portion of field of view 414. In other words, the light source 408 may be configured to switch from providing continuous light to providing stroboscopic light, and vice versa, in response to control signals received from surgical console 101 or another device.

For example, the endo-illumination device 400 may be configured to provide continuous illumination (e.g., bright, background, broad-wavelength band, narrow-wavelength band, and/or white light) to illuminate the surgical field during procedures of the surgical operation where stroboscopic illumination is not used and/or beneficial. In some embodiments, the endo-illumination device 400 can selectively (e.g., at different times) provide only continuous light, only stroboscopic illumination, and/or combinations of continuous light and stroboscopic illumination (e.g., continuous light of one wavelength (or wavelength band) and stroboscopic illumination of a different (e.g., non-overlapping) wavelength (or wavelength band)).

In the embodiments of FIGS. 4A and 4B, when endo-illumination device 400 provides stroboscopic illumination, the microscopy illuminator of visualization tool 420 may be turned off or simultaneously provide continuous light with either the same intensity (i.e., same as when no stroboscopic illumination is provided) or a diminished intensity.

External Stroboscopic Illumination

FIGS. 5A and 5B illustrate a cross-sectional view of an eye 530 during exemplary ophthalmic surgical procedures where a surgical probe (e.g., tool 103), an external stroboscopic illumination device 500, an endo-illumination device 400, and a visualization tool 420 are utilized. In FIG. 5A, the surgical probe is a vitrector 203 that is used during a vitrectomy procedure while FIG. 5B shows an example phacoemulsification probe 303 used during cataract surgery. In the embodiments of FIGS. 5A and 5B, the endo-illumination device 400 of FIGS. 4A and 4B is configured to provide continuous illumination while stroboscopic illumination is provided by external stroboscopic illumination device 500 at least during certain procedures of the surgical operations performed in FIGS. 5A and 5B. In certain embodiments, the stroboscopic illumination device 500 illuminates the portion of field of view 514 with stroboscopic light at least during certain procedures during the surgical operation performed using vitrector 203 (as illustrated in FIG. 5A) or phacoemulsification probe 303 (as illustrated in FIG. 5B).

More specifically, the external stroboscopic illumination device 500 may illuminate the surgical field with pulses of light (e.g., broad-wavelength band light, narrow-wavelength band light) with a certain illumination frequency. The external stroboscopic illumination device 500 may include a spot illuminator, an optical fiber, a flash LED, a pulsed LED, a laser diode, a pulsed laser, a flashtube (e.g., a xenon flashtube, a krypton flashtube, an argon flashtube, a neon flashtube, etc.), other suitable components, and/or combinations thereof that provide pulses of light.

As shown, the external stroboscopic illumination device 500 is external to the eye 530 and, therefore, the emitted stroboscopic light 512 enters the eye through the cornea and allows for the interior of the eye 530 to be viewed with the visualization tool 420. The external stroboscopic illumination device 500 is coupled to a light source 508 that functions as a stroboscopic illumination source for the external stroboscopic illumination device 500. Although not shown, in certain embodiments, the external stroboscopic illumination device 500 and/or its light source 508 may be mounted on the visualization tool 420 and/or be integral parts of visualization tool 420. In certain other embodiments, the external stroboscopic illumination device 500 and/or its light source 508 may be distinct from the visualization tool 420.

In certain embodiment, the external stroboscopic illumination device 500 may define an external stroboscopic illumination axis that is not parallel to a visualization axis of the visualization tool 420. In some other embodiments, the external stroboscopic illumination device 500 may be coupled to the visualization tool such that visualization axis and the external stroboscopic illumination axis are parallel. The external stroboscopic illumination axis may intersect with the visualization axis at or near the site of ocular interactions (e.g., within the field of view of the visualization tool 420). In some embodiments, the angle between the visualization axis and the external stroboscopic illumination axis may be selected to provide desired visualization results (e.g., reduced glare, selected polarization configurations, etc.). It should be appreciated that larger angles (e.g., greater than 45°) between the visualization axis and the external stroboscopic illumination axis may result in poor stroboscopic illumination. In some embodiments, the angle between the visualization axis and the external stroboscopic illumination axis may be about 15° to about 30°, or about 20° to about 25°. Providing stroboscopic illumination at such an angle to the visualization axis may provide off-axis dark-field illumination. Off-axis dark-field illumination is a kind of dark field illumination which further enhances the visibility of images provided by visualization tool 420. For example, off-axis dark-field illumination may be utilized to visualize liquid flow processes, especially for fluids of varying density.

In certain embodiments, the light source 508 may be an integral part of surgical console 101, which controls the surgical probes shown in FIGS. 5A and 5B (e.g., vitrector 203, phacoemulsification probe 303, etc.). In certain other embodiments, the light source 508 is an independent unit and not an integral part of surgical console 101. In such embodiments, as described in further detail below, the light source 508 may be communicatively coupled to (e.g., wired or wirelessly) surgical console 101.

Regardless of whether or not light source 508 is an integral part of surgical console 101, in certain embodiments, the surgical console 101 may control the operations of light source 508. Controlling the operations of lights source 508 includes controlling the frequency with which light source 508 provides stereoscopic illumination for illuminating the surgical field through external stroboscopic illumination device 500. Controlling the frequency of the light source 508 may include synchronizing the frequency of the light source 508 with a driving frequency with which the surgical probe is operated at least during certain procedures of a corresponding surgical operation. Controlling the operations of light source 508 may also include sending control signals to light source 508 to cause it to switch from providing stroboscopic illumination to providing continuous illumination and vice versa.

Note that when the external stroboscopic illumination device 500 provides stroboscopic illumination, the additional sources of illumination (e.g., the microscopy illuminator of visualization tool 420, the optional endo-illumination device 400, etc.) may either be entirely turned off or simultaneously provide continuous light with either the same intensity (i.e., same as when no stroboscopic illumination is provided) or a diminished intensity.

Microscopy Stroboscopic Illuminator

FIGS. 6A and 6B illustrate a cross-sectional view of an eye 630 during exemplary ophthalmic surgical procedures where a surgical probe (e.g., tool 103), an endo-illumination device 400, and a visualization tool 420 are utilized. In FIG. 6A, the surgical probe is a vitrector 203 that is used during a vitrectomy procedure while FIG. 6B shows an example phacoemulsification probe 303 used during cataract surgery. As previously discussed, visualization tool 420 may comprise a microscopy illuminator that is configured to provide continuous illumination. In one example, this previously-discussed microscopy illuminator may be adapted or reconfigured to be a stroboscopic illumination source. In another example, in addition to this previously-discussed microscopy illuminator that is configured to provide continuous illumination, visualization tool 420 may include (e.g., internally integrated) a stroboscopic microscopy illuminator 600. In yet another example, visualization tool 420 may comprise a stroboscopic microscopy illuminator 600 in lieu of the previously-discussed microscopy illuminator.

In certain embodiments, the stroboscopic microscopy illuminator 600 illuminates the portion of field of view 614 with stroboscopic light at least during certain procedures during a surgical operation (e.g., performed using vitrector 203 (as illustrated in FIG. 6A) or phacoemulsification probe 303 (as illustrated in FIG. 6B)). In certain embodiments, stroboscopic microscopy illuminator 600 may be provided by disposing a ring of LEDs around the central axis of attachment 424. In certain other embodiments, one or more stroboscopic LEDs may be positioned proximally with respect to objective 422. In certain embodiments, the stroboscopic microscopy illuminator 600 may define an illumination axis that is not parallel to a visualization axis of the visualization tool 420. In some other embodiments, the illumination axis may be parallel or coaxial with the visualization axis.

In the embodiments of FIGS. 6A and 6B, when stroboscopic microscopy illuminator 600 provides stroboscopic illumination, the additional sources of illumination (e.g., endo-illumination device 400, etc.) may either be entirely turned off or simultaneously provide continuous light with either the same intensity (i.e., same as when no stroboscopic illumination is provided) or a diminished intensity.

Time Sequence

FIGS. 7A-7L illustrate an exemplary stroboscopic visualization of an interaction between energy emitted from the tip of a surgical probe and surrounding fluid. FIGS. 7A-7L include a collection of images taken from a video made with stroboscopic illumination. In the illustrated example, the surgical probe is a laser having a driving frequency of about 1500 Hz. The stroboscopic illumination frequency is 1499 Hz. As illustrated, stroboscopic illumination allows visualization of formation (see FIG. 7A), expansion (see FIGS. 7B and 7C), oscillation (see FIGS. 7D and 7E), translation (see FIG. 7F), and disintegration (see FIGS. 7G-7L) of a bubble in ocular fluid. Other interactions that may be expected to be visualized with stroboscopic illumination include: angular radiation pattern of the ultrasonic waves around the phaco tip, the development of cavitation bubbles around the phaco tip, acoustic streaming around the phaco tip, the sledgehammer emulsification effect of the phaco tip, movement of phaco tip, movement of different components of the phaco handpiece, oscillations and/or bending of the balanced phaco tip (for example, see U.S. Pat. No. 10,258,505), lens fragmentation and/or fragment movement in the anterior chamber of the eye, movement of vitreous during vitrectomy, etc.

Frequency Coordination

Many ophthalmic surgical procedures involve ocular interactions that happen too fast to be visualized with the naked eye or with typical video cameras. For example, common ophthalmic surgical tools (e.g., tool 103 discussed above) operate at high frequencies that may result in high-speed ocular interactions. Table 1 identifies common ophthalmic surgical probe types and typical operational/driving frequency ranges for each.

TABLE 1

| Probe Type | Typical Driving Frequency |
|---|---|
| Vitrectomy blade | 175-225 Hz |
| Picosecond infrared laser | 0.8-1.2 kHz |
| Ultrasonic vitrector | 20-30 kHz |
| Ultrasonic phaco | 30-50 kHz |
| Femtosecond laser-assisted cataract surgery laser | 50-200 kHz |
| Femtosecond flap cutters | 100-500 kHz |
| Lasik excimer lasers | 100-1000 pulse/second |

According to embodiments of the present disclosure, the driving frequency of the surgical probe and the illumination frequency of the stroboscopic illumination source may be coordinated. Specifically, the driving frequency of the surgical probe and the illumination frequency of the stroboscopic illumination source may be coordinated to be close, but not equal. In such circumstances, the surgeon viewing the procedure through a surgical microscope sees the illuminated interaction occurring at a frequency equal to the absolute value of the difference between the illumination frequency and the driving frequency. For example, if the driving frequency is 125 Hz, and the illumination frequency is either 115 Hz or 135 Hz, the illuminated interaction would appear to have a frequency of 10 Hz (absolute value of 125 Hz-115 Hz and 125 Hz-135 Hz). As another example, if the driving frequency is 200 Hz, and the illumination frequency is either 199 Hz or 201 Hz, the illuminated interaction would appear to have a frequency of 1 Hz. In other words, the illuminated interaction would appear to have been slowed by a factor of 200. As another example, if the driving frequency is 1500 Hz, and the illumination frequency is either 1499 Hz or 1501 Hz, the illuminated interaction would appear to have a frequency of 1 Hz. In the case with an illumination frequency of 1499 Hz, the observer will see a forward-moving process, while in the case with an illumination frequency of 1501 Hz, the process will appear to move backwards. In other words, the illuminated interaction would appear to have been slowed by a factor of 1500.

The sign/polarity of the difference between the driving frequency and the illumination frequency determines whether the illuminated interaction appears to move forward (in time) or in reverse. The physiological difference between reverse and forward motion of the ocular tissue may or may not be distinguishable to the surgeon. In some embodiments, the surgeon may have a preference to view the tissue motion in a forward manner or in reverse. The surgeon may control the magnitude and the sign/polarity of the frequency difference to achieve a desired visualization.

Because the ocular tissue appears to move at a slower speed under stroboscopic illumination, the surgeon can more clearly see the amplitude and shape of the interaction, and thus carry out the surgical procedure accordingly. The apparent slower motion also allows for the surgeon to confirm that the probe is functioning as intended. Without stroboscopic illumination, for example, the pulsed energy of the probe is typically too quick for the surgeon to visualize. Note that if the illumination frequency is set to be equal to the driving frequency, it may result in an appearance of the ocular tissue being stationary. By changing the phase between the illumination frequency and the driving frequency (e.g. manually), the surgeon can "freeze" the image at any phase of the periodic tip-tissue interaction.

The stroboscopic illumination frequency can be coordinated to be at sub-harmonics of the driving frequency (i.e., illumination frequency=driving frequency/N, where N=2, 3, 4 etc.).

The stroboscopic illumination frequency may be automatically coordinated with the driving frequency of the surgical probe. For example, many phaco probes may change the driving frequency during an operation by a few percent in response to the variation of the lenticular hardness. The stroboscopic illumination frequency may be automatically adjusted to the driving frequency of the phaco probe as it changes during the operation.

The stroboscopic illumination source may be characterized by both an illumination frequency and a light pulse duration. The pulse duration may at least in part determine the temporal resolution of the stroboscopic images. For example, a laser diode can have light pulse durations as short as a few nanoseconds. Utilizing such a laser diode as a stroboscopic illumination source provides a temporal resolution of the strobed image as short as a few nanoseconds.

In addition to coordinating relative frequencies, coordinating the oscillations of the probe with the stroboscopic illumination source may include coordinating the phase of each. The phase difference between the probe and the stroboscopic illumination source can be accurately controlled electronically. By keeping the phase difference between the stroboscopic illumination source and the probe constant, the surgeon will see a "time-frozen" image of the surgical process at a certain phase of the process.

Wavelengths and Illumination Configurations

In some embodiments, as described above, a stroboscopic illumination source may be utilized in conjunction with a continuous illumination source. In some embodiments, the wavelength of light (or band of wavelengths) utilized in the stroboscopic illumination source may differ from the wavelength (or band of wavelengths) associated with the, e.g., simultaneously provided, continuous illumination. In some embodiments, the polarization of light utilized in the stroboscopic illumination source may differ from the polarization associated with the, e.g., simultaneously provided, continuous illumination In some embodiments In some embodiments, the stroboscopic illumination is positioned and/or configured to provide forward illumination of one or more elements in the field of view of the visualization tool. For example, the stroboscopic illumination may be positioned and/or configured to reflect light off of the one or more elements in the field of view and into the objective of the visualization tool. In some embodiments, the stroboscopic illumination is positioned and/or configured to provide backward illumination of one or more elements in the field of view of the visualization tool. For example, the stroboscopic illumination may be positioned and/or configured to transmit light through the one or more elements (e.g., clear fluid) in the field of view (while being reflected or absorbed by one or more other elements) and then directly (without any reflections) into the objective of the visualization tool.

In some embodiments, the stroboscopic illumination is positioned and/or configured to provide reflective illumination of one or more elements in the field of view of the visualization tool. For example, the stroboscopic illumination may be positioned and/or configured to transmit light through one or more elements (e.g., clear fluid) in the field of view (while being reflected or absorbed by one or more other elements), to a back-screen (e.g., a retina), and then to reflect from the back-screen back towards and into the objective of the visualization tool. In some embodiments, the stroboscopic illumination is positioned and/or configured to provide retro-reflective illumination of one or more elements in the field of view of the visualization tool. For example, the stroboscopic illumination may be positioned and/or configured to transmit light to a back-screen (e.g., a retina), then to reflect from the back-screen back towards and through one or more elements (e.g., clear fluid) in the field of view (while being reflected or absorbed by one or more other elements), and then directly (without any reflections) into the objective of the visualization tool.

Operation of the Stroboscopic Illumination Source

Figure 8:
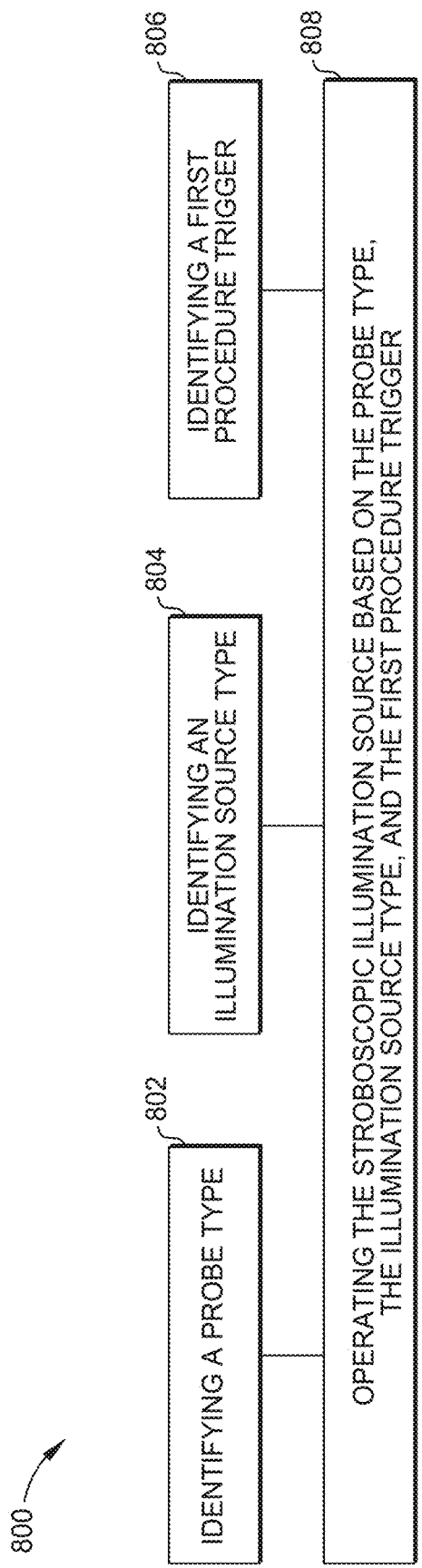
FIG. 8 illustrates an example exemplary process flow for visualization of interactions within or associated with an ocular space of an eye with stroboscopic illumination, in accordance with certain embodiments.

FIG. 8 illustrates exemplary operations 800 for use by a surgical console (e.g., surgical console 101, surgical console 900) to directly or indirectly control the operations of a stroboscopic illumination source during a surgical operation. The process flow may begin at one or more of operations 802, 804, and 806. Note that operations 802, 804, and 806 do not necessarily correspond to different steps that have to be performed individually and/or in a particular order. In certain embodiments, one or more of operations 802, 804, and 806 may be performed as one step. In certain embodiments, one or more of operations 802, 804, and 806 are optional and can be omitted. Further the order of operations 802, 804, and 806 may be different in various implementations. Note that any one of operations 802, 804, and 806 may act as a trigger for surgical console 900 to control (e.g., set or switch) operating states of a stroboscopic illumination source that the surgical console 900 is communicatively coupled with.

At operation 802, a control module (e.g., procedure flow module 926 of control module 901 in FIG. 9) of surgical console 900 may identify a procedure trigger associated with a surgical operation. In certain embodiments, surgical console 900 may be configured with multiple types of surgical probes for allowing a surgeon to operate multiple corresponding surgical operations. For example, surgical console 900 may be configured with one or more of the previously-discussed surgical probes (e.g., vitrector, phacoemulsification probe, pIRL, etc.) for performing one or more of the previously-discussed surgical operations (e.g., vitreo-retinal surgery, cataract surgery, LASIK surgery, etc.). Each of these surgical operations may include a variety of steps or procedures that need to be completed. Surgical console 900 may, therefore, be configured with information and workflows relating to each of these surgical operations. As an example, surgical console 900 may be configured with a surgical operation profile (e.g., surgical operations profile 924) for each of the surgical operations the console is configured to perform. In one example, a surgical operation profile may correspond to cataract surgery while another surgical operations profile may correspond to a type of vitreo-retinal surgery, and so on. Each of the surgical profiles may indicate a workflow of a number of procedures.

Prior to starting a surgical operation, a user (surgeon or technician) may the use the user interface of surgical console 900 to select the surgical operation from among a number of surgical operations presented on the user interface. In response, surgical console 900 may execute a corresponding surgical operation profile, which may then cause surgical console 900 to display a workflow of all the procedures that need to be performed for completing the cataract surgery. The user may then select a first procedure in the workflow using the user interface, which may cause surgical console 900 to enter a mode that allows the surgeon to perform the first procedure. Once the first procedure is complete, the user may select the second procedure in the workflow, which may cause surgical console 900 to enter a mode that allows the surgeon to perform the second procedure, and so on, until the surgical operation is complete.

For each of the previously-discussed surgical operations, there may be at least one or more procedures during which the use of stroboscopic illumination may be advantageous. For example, during cataract surgery, the surgeon may benefit from the use of stroboscopic illumination when performing a procedure for emulsifying the lens. In such an example, as further described in relation to operations 808, when the user selects the lens emulsification procedure (e.g. phacoemulsification, laser lens emulsification) in the workflow, the surgical console 900 is configured to identify that the lens emulsification procedure has been triggered and, therefore, control the operations of the stroboscopic illumination source accordingly. When the surgeon completes the lens emulsification procedure, the user may select the next procedure, which causes the surgical console 900 to identify a procedure trigger associated with the next procedure. Identifying a procedure trigger associated with the next procedure indicates to surgical console 900 that the previous procedure, e.g., the lens emulsification procedure, is complete and may, therefore, cause surgical console 900 to change the operations of the stroboscopic illumination source, as further described in relation to operations 808.

In another example, during a vitreo-retinal surgery, the surgeon may benefit from the use of stroboscopic illumination when cutting and removing the vitreous. In such an example, when the user selects the vitrectomy procedure in the workflow, the surgical console 900 is configured to identify that the vitrectomy procedure has been triggered and, therefore, control the operations of the stroboscopic illumination source accordingly, and so on. Note that, in certain embodiments, surgical console 900 may be configured with only one type of surgical operation, in which case the control module is able to automatically and by default determine that the workflow associated with the surgical operation.

At operation 804, a surgical probe type may be identified by the control module (e.g., procedure flow module 926 of FIG. 9) at the surgical console 900. In certain embodiments, the control module may identify the surgical probe type based on the surgical operation and/or the latest procedure trigger selected by the technician. For example, if the user has selected the vitreo-retinal surgical operation and the latest procedure trigger corresponds to vitrectomy, then the control module may identify that the appropriate probe for this surgical procedure is a vitrector. The control module may then retrieve the corresponding probe profile from memory to be able to operate the probe based on user input, etc.

In another example, if the technician has selected cataract surgery and the latest procedure trigger corresponds to lens emulsification, then the control module may identify that the appropriate probe for this surgical procedure is a phacoemulsification probe. In certain embodiments, the control module may identify the probe type based on user input that indicates a selection of the probe type from among a number of probe types. In certain embodiments, surgical console 900 may be configured with only one type of probe, in which case the control module automatically and by default identifies the corresponding probe type. In certain embodiments, the control module may identify the probe type through some other mechanism that is not described here but is well known to one of ordinary skill in the art.

At operation 806, an illumination source type may be identified. In some embodiments, the control module (e.g., illumination management module 928) may identify illumination source type based on the surgical operation and/or the latest procedure trigger selected by the technician. For example, if the user has selected the vitreo-retinal surgical operation and the latest procedure trigger corresponds to vitrectomy, then the control module may identify that stroboscopic illumination should be used during this procedure. Information as to what type of illumination should be used during which procedure of a surgical operation may be indicated by a corresponding surgical operation profile and/or a probe type profile. For a certain procedure, the control module may also be configured with information on how to operate any continuous illumination source. For example, while stroboscopic illumination is provided during vitrectomy, the control module may be configured to switch off any continuous illumination source.

At operation 808, the surgical console sets or switches operating states of the stroboscopic illumination source based on an indication. The indication may include user input received by surgical console 900 or be based on the identified probe type, illumination source type, and/or procedure trigger type. For example, as further described below with reference to FIG. 9, an illumination management module 928 of surgical console 900 may be configured to control certain aspects of the stroboscopic illumination source (e.g., illumination source 914 or illumination source 916). For example, the stroboscopic illumination source may have one or more operating states, including "on" and "off". The illumination management module 928 of surgical console 900 may be configured to control switching the stroboscopic illumination source from one state to another state. As another example, the stroboscopic illumination system may operate at one or more frequency settings. The illumination management module 928 of surgical console 900 may be configured to adjust the frequency setting of the stroboscopic illumination source. The illumination management module 928 of surgical console 900 may also be configured to adjust the frequency of the stroboscopic illumination source based on an indication of the real-time driving frequency of the surgical probe. An indication of the real-time driving frequency of the surgical probe may be received by the illumination management module 928 from a driver circuit that drives the surgical probe or through another mechanism, as may be known to one of ordinary skill in the art. As another example, the stroboscopic illumination source may operate at one or more light wavelengths (or bands of wavelengths). The illumination management module 928 of surgical console 900 may be configured to control adjusting the wavelength setting of the stroboscopic illumination source.

The illumination management module 928 of surgical console 900 may be configured to control certain aspects of the stroboscopic illumination source in response to one or more inputs. For example, the surgeon may directly input (e.g., via I/O device interface 909) a set of desired aspects (e.g., turn "on" the stroboscopic illumination source at an illumination frequency of 1499 Hz and a wavelength band of 570 nm-590 nm). As another example, the illumination management module 928 may receive inputs from other components of the surgical console 900 (e.g., procedure flow module 926). The illumination management module 928 may utilize the inputs from the other components with a mapping for specified aspect settings of the stroboscopic illumination source. The mapping may include mappings between one or more of the following: surgical probe, stroboscopic illumination, surgical operation, procedure and/or procedure triggers, probe frequency, available stroboscopic illumination frequencies, continuous light wavelength, available stroboscopic illumination wavelengths, continuous light polarization, available stroboscopic illumination polarizations, etc.

The described stroboscopic illumination source may provide beneficial illumination for time-resolved visualization of the surgical field of a variety of ophthalmic operations and a variety of procedures included in each operation. For example, applicable ophthalmic operations may include: vitreoretinal surgery, pIRL-based cataract surgery, phaco surgery, femtosecond laser-assisted cataract surgery (FLACS), femtosecond flap making, LASIK, and excimer laser ablation of the cornea. Moreover, applicable procedures of such operations may include: create an incision, displace and/or replace a flap, cut and/or break-down vitreous fluid, aspirate vitreous fluid, break-down and/or emulsification of a cataract, aspirate a cataract, disintegration of a lens, removal of lens particles, ablation of a cornea, and removal of scar tissue and/or other tissue.

Transitions between procedures of an operation may be accompanied and/or identified by several triggers related to surgical illumination. Likewise, during any particular procedure, certain operational conditions may indicate a trigger for a desired change in aspects of the procedure related to surgical illumination. Examples of potential transitions between procedures include: the surgeon may switch from manipulation of one type of tool to another type of tool. Such a switch may indicate a trigger for switching type(s) and/or aspect(s) of illumination. As further examples of potential transitions, the surgeon may change aspect(s) of the tool being utilized, such as driving frequency, power, wavelength, probe position, and/or probe angle. As further examples, a surgical console control module 901 may detect an operational condition (e.g., proximity of probe tip to retina, hardness of ocular matter proximate the probe tip) that indicates a desired change in aspect(s) of the tool being utilized, such as driving frequency, power, and/or wavelength. As further examples, the surgical console control module 901 may change aspect(s) of the tool being utilized in response to transitions between procedures. Any of these examples may alone or in combination indicate a trigger for switching type(s) and/or aspect(s) of illumination.

Figure 9:
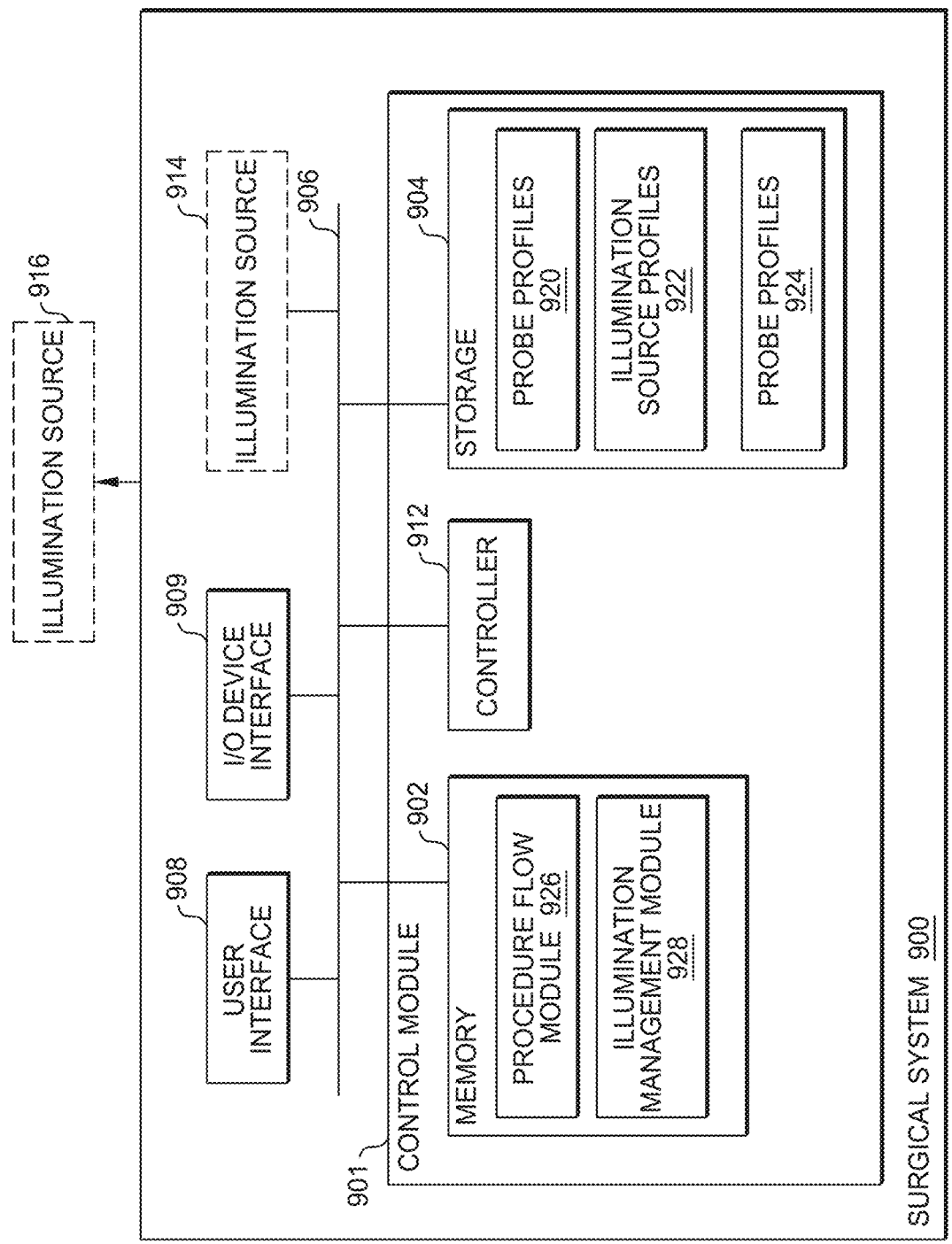
FIG. 9 an exemplary diagram of a surgical console, in accordance with certain embodiments.

FIG. 9 illustrates an exemplary diagram of the surgical console 900 of FIG. 1, according to embodiments disclosed herein. As shown, surgical console 900 includes, without limitation, a control module 901, user interface display 908 (e.g., display 109 of FIG. 1), an interconnect 906, and at least one I/O device interface 909, which may allow for the connection of various I/O devices (e.g., keyboards, displays, mouse devices, pen input, etc.) to surgical console 900. Surgical console 900 may also include an illumination source 914 (e.g., a continuous illumination source and/or a stroboscopic illumination source). In some embodiments, surgical console 900 may operatively couple to an illumination source 916 (e.g., a continuous illumination source and/or a stroboscopic illumination source).

Control module 901 includes a controller (e.g., CPU 912), memory 902, and storage 904. The CPU 912 is configured to retrieve and execute programming instructions stored in the memory 902. Similarly, CPU 912 may retrieve and store application data residing in memory 902. Interconnect 906 transmits programming instructions and application data, among CPU 912, I/O device interface 909, user interface 908, memory 902, and the storage 904, illumination source 914, illumination source 916, etc. The CPU 912 may include a single CPU, multiple CPUs, a single CPU having multiple processing cores, and the like. The memory 902 may be random access memory, and the storage 904 may be a disk drive. Moreover, the memory 902 and/or the storage 904 may be any type of a readily available memory, such as random access memory (RAM), read only memory (ROM), floppy disk, hard disk, solid state, flash memory, magnetic memory, or any other form of digital storage, local or remote. In certain embodiments, the memory 902 and/or the storage 904 include instructions, which when executed by the CPU 912, cause coordination of the driving frequency of the probe and the illumination frequency of the stroboscopic illumination source. In certain embodiments, the CPU 912, the memory 902, and the storage 904 may be the main processor and memory of surgical console 101 (see FIG. 1), which may implement or include surgical console 101.

As shown, storage 904 includes probe profiles 920 representing various probe types, as previously described with reference to tool 103 of FIG. 1. Storage 904 also includes illumination source profiles 922 representing various stroboscopic illumination source types, as previously described.

Memory 902 includes a procedure flow module 926 for adjusting the aspects of the probe (e.g., frequency or power) during the ophthalmic surgical procedure, as described in the embodiments herein. In addition, memory 902 includes an illumination management module 928 that interfaces with illumination source 914 and/or illumination source 916.

In an embodiment, an ophthalmic system for visualization of interactions between ocular matter and a probe tip of a probe within or in contact with an ocular space of an eye includes: a visualization tool having a field of view that includes at least a portion of the ocular space of the eye where the probe tip interfaces with the ocular matter; and a stroboscopic illumination source configured to stroboscopically illuminate at least the portion of the field of view at an illumination frequency.

In one or more embodiments disclosed herein, the visualization tool comprises one or more of: a microscope; a digital microscope; and a camera.

In one or more embodiments disclosed herein, the system also includes a surgical console configured to: drive the probe with a driving frequency to produce energy at the probe tip; and coordinate the illumination frequency with the driving frequency.

In one or more embodiments disclosed herein, the energy comprises one or more of: light energy; ultrasonic energy; energy causing breaking-down of the ocular matter; and energy causing movement in the ocular matter.

In one or more embodiments disclosed herein, coordinating the illumination frequency with the driving frequency comprises maintaining the illumination frequency in a range of about 1 Hz less than the driving frequency to about 5 Hz less than the driving frequency.

In one or more embodiments disclosed herein, the driving frequency changes in response to one or more procedure triggers.

In one or more embodiments disclosed herein, the probe includes: a picosecond infrared laser probe; a femtosecond laser probe; a vitrectomy probe; a phacoemulsification probe; an excimer laser; or a flap cutter.

In one or more embodiments disclosed herein, the stroboscopic illumination source includes any of: a light-emitting diode (LED); a laser diode; a flashtube; a polarized light source; a broad-wavelength band light source; a narrow-wavelength band light source; and an optical fiber positioned in the ocular matter.

In one or more embodiments disclosed herein, the stroboscopic illumination source is configured to illuminate the portion of the field of view with one or more of: endoscopic illumination; external-to-the-eye illumination; forward illumination; backward illumination; angled illumination; reflective illumination; and co-illumination with a second illumination source.

In one or more embodiments disclosed herein, the stroboscopic illumination source defines an illumination axis, the visualization tool defines a visualization axis, and the illumination axis crosses the visualization axis in the portion of the field of view at an angle.

In one or more embodiments disclosed herein, the angle is about 15° to about 30°.

In one or more embodiments disclosed herein, the system also includes a controller configured with instructions to: identify a probe type of the probe; identify an illumination source type of the stroboscopic illumination source; identify a procedure trigger; and operate the stroboscopic illumination source based on the probe type, the illumination source type, and the procedure trigger.

In one or more embodiments disclosed herein, the controller being configured with instructions to operate the stroboscopic illumination source comprises the controller being configured with instructions to alter a state of the illumination source.

In one or more embodiments disclosed herein, the state comprises "on" or "off."

In one or more embodiments disclosed herein, the state comprises a specified setting of the illumination frequency.

In one or more embodiments disclosed herein, operating the stroboscopic illumination source comprises: driving the probe with a driving frequency; and coordinating the illumination frequency with the driving frequency.

In one or more embodiments disclosed herein, the system also includes a second illumination source configured to illuminate the portion of the field of view, wherein the second illumination source is a continuous light source.

In one or more embodiments disclosed herein, the stroboscopic illumination source produces light of a first wavelength band, the second illumination source produces light of a second wavelength band, and the first wavelength band is at least partially outside of the second wavelength band.

In an embodiment, a method of operating a stroboscopic illumination source during an ophthalmic surgical procedure includes: identifying an illumination source type of the stroboscopic illumination source, wherein the stroboscopic illumination source is configured to stroboscopically illuminate at least a portion of a field of view of a visualization tool at an illumination frequency; identifying a probe type of a probe used for the ophthalmic surgical procedure, the probe having a probe tip that is configured to contact ocular matter in the portion of the field of view of the visualization tool; identifying a first procedure trigger corresponding to a first operation of the ophthalmic surgical procedure; and operating the stroboscopic illumination source based on the probe type, the illumination source type, and the first procedure trigger.

In one or more embodiments disclosed herein, operating the stroboscopic illumination source comprises: driving the probe with a driving frequency; and coordinating the illumination frequency with the driving frequency.

In one or more embodiments disclosed herein, driving the probe produces energy at the probe tip, the energy including one or more of: light energy; ultrasonic energy; energy causing break-down of the ocular matter; and energy causing movement in the ocular matter.

In one or more embodiments disclosed herein, the first procedure trigger is indicative of a start of the first operation, and operating the stroboscopic illumination source comprises switching the stroboscopic illumination source "on" in response to identifying the first procedure trigger.

In one or more embodiments disclosed herein, the method also includes identifying a second procedure trigger, wherein: the second procedure trigger is indicative of an end of the first operation, and operating the stroboscopic illumination source comprises switching the stroboscopic illumination source "off" in response to identifying the second procedure trigger.

In one or more embodiments disclosed herein, the first operation includes: breaking-down and removing a lens in the ocular space using the probe; or cutting and aspirating vitreous in the ocular space using the probe.

In one or more embodiments disclosed herein, the first operation comprises at least one of: breaking-down a cataract; removing a cataract; removing vitreous; and removing scar tissue;

In one or more embodiments disclosed herein, operating the stroboscopic illumination source comprises altering a state of the stroboscopic illumination source.

In one or more embodiments disclosed herein, altering the state of the stroboscopic illumination source comprises switching the stroboscopic illumination source "on" at least in part based on the first procedure trigger.

In one or more embodiments disclosed herein, the method also includes identifying a second procedure trigger corresponding to a second operation of the ophthalmic surgical procedure, wherein altering the state of the stroboscopic illumination source comprises switching the stroboscopic illumination source "off" at least in part based on the second procedure trigger.

In one or more embodiments disclosed herein, the method also includes upon switching the stroboscopic illumination source "off:" continuing to utilize a second illumination source to illuminate the portion of the field of view; or switching "on" the second illumination source.

In one or more embodiments disclosed herein, operating the stroboscopic illumination source comprises operating the stroboscopic illumination source according to a specified setting of the illumination frequency, wherein the specified setting is determined based on a mapping between the specified setting and at least one of the first procedure trigger and the probe type.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An ophthalmic system for visualization of interactions between ocular matter and a probe tip of a probe within or in contact with an ocular space of an eye, comprising:
    a visualization tool having a field of view that includes at least a portion of the ocular space of the eye where the probe tip interfaces with the ocular matter, wherein the visualization tool defines a visualization axis; and
    a stroboscopic illumination source configured to stroboscopically illuminate at least the portion of the field of view at an illumination frequency, wherein the stroboscopic illumination source defines an illumination axis, wherein the illumination axis crosses the visualization axis in the portion of the field of view at an angle of about 15° to about 30°.

2. The system of claim 1, wherein the visualization tool comprises one or more of:
    a microscope;
    a digital microscope; and
    a camera.

3. The system of claim 1, further comprising a surgical console configured to:
    drive the probe with a driving frequency to produce energy at the probe tip; and
    coordinate the illumination frequency with the driving frequency.

4. The system of claim 3, wherein the energy comprises one or more of:
    light energy;
    ultrasonic energy;
    energy causing breaking-down of the ocular matter; and
    energy causing movement in the ocular matter.

5. The system of claim 3, wherein coordinating the illumination frequency with the driving frequency comprises maintaining the illumination frequency in a range of about 1 Hz less than the driving frequency to about 5 Hz less than the driving frequency.

6. The system of claim 1, wherein the probe comprises:
    a picosecond infrared laser probe;
    a femtosecond laser probe;
    a vitrectomy probe;
    a phacoemulsification probe;
    an excimer laser; or
    a femtosecond flap cutter.

7. The system of claim 1, wherein the stroboscopic illumination source is configured to illuminate the portion of the field of view with one or more of:
    endoscopic illumination;
    external-to-the-eye illumination;
    forward illumination;
    backward illumination;
    angled illumination;
    trans-scleral illumination;
    reflective illumination; and
    co-illumination with a second illumination source.

* * * * *